United States Patent
Li et al.

(10) Patent No.: US 9,988,371 B2
(45) Date of Patent: Jun. 5, 2018

(54) BENZIMIDAZOLE ANALOGUES AND RELATED METHODS

(71) Applicants: The Arizona Board of Regents, on Behalf of the University of Arizona, Tucson, AZ (US); Universita' Federico II, Naples (IT)

(72) Inventors: Hong-yu Li, Tucson, AZ (US); Brendan Frett, Tucson, AZ (US); Massimo Santoro, Naples (IT); Francesca Carlomagno, Naples (IT)

(73) Assignees: THE ARIZONA BOARD OF REGENTS ON BEHALF OF THE UNIVERSITY OF ARIZONA, Tucson, AZ (US); UNIVERSITA' FEDERICO II (IT)

( * ) Notice: Subject to any disclaimer, the term of this patent is extended or adjusted under 35 U.S.C. 154(b) by 0 days. days.

(21) Appl. No.: 15/315,490

(22) PCT Filed: Jun. 3, 2015

(86) PCT No.: PCT/US2015/033962
§ 371 (c)(1),
(2) Date: Dec. 1, 2016

(87) PCT Pub. No.: WO2015/187818
PCT Pub. Date: Dec. 10, 2015

(65) Prior Publication Data
US 2017/0101401 A1    Apr. 13, 2017

Related U.S. Application Data

(60) Provisional application No. 62/007,321, filed on Jun. 3, 2014.

(51) Int. Cl.
| | |
|---|---|
| *C07D 413/12* | (2006.01) |
| *C07D 413/14* | (2006.01) |
| *A61K 31/422* | (2006.01) |
| *A61K 45/06* | (2006.01) |
| *A61K 31/4439* | (2006.01) |
| *A61K 31/5377* | (2006.01) |
| *A61K 31/506* | (2006.01) |
| *C12N 9/12* | (2006.01) |

(52) U.S. Cl.
CPC .......... *C07D 413/14* (2013.01); *A61K 31/422* (2013.01); *A61K 31/4439* (2013.01); *A61K 31/506* (2013.01); *A61K 31/5377* (2013.01); *A61K 45/06* (2013.01); *C07D 413/12* (2013.01); *C12N 9/12* (2013.01); *C12Y 207/10002* (2013.01)

(58) Field of Classification Search
CPC ........................... C07D 413/12; C07D 413/14
See application file for complete search history.

(56) References Cited

U.S. PATENT DOCUMENTS

| | | | |
|---|---|---|---|
| 8,030,311 | B2 | 10/2011 | Bold et al. |
| 2003/0225054 | A1 | 12/2003 | Duan |
| 2012/0135953 | A1 | 5/2012 | Mc Gowan et al. |
| 2012/0184561 | A1 | 7/2012 | Bold et al. |
| 2014/0107172 | A1 | 4/2014 | Vandyck et al. |

FOREIGN PATENT DOCUMENTS

| | | |
|---|---|---|
| EP | 1904494 B1 | 12/2010 |
| WO | 2006/108640 A1 | 10/2006 |
| WO | WO-2013/019682 A1 * | 2/2013 |

OTHER PUBLICATIONS

Chemical Abstracts Registry No. 1319089-14-9, indexed in the Registry file on Aug. 17, 2011.*
Grant, R., Grant, C. (1987). Grant & Hackh's Chemical Dictionary (5$^{th}$ ed.). New York, NY: McGraw-Hill, p. 313.*
Golub et al., Science, vol. 286, Oct. 15, 1999, pp. 531-537.*
Vourloumis et al., "Solid-phase synthesis of benzimidazole libraries biased for RNA targets", Tetrahedron Letters, 2003, vol. 44, pp. 2807-2811.
PCT International Search Report and the Written Opinion, Application No. PCT/US2015/033962 filed Jun. 3, 2015, dated Aug. 17, 2015.

* cited by examiner

*Primary Examiner* — Laura L. Stockton
(74) *Attorney, Agent, or Firm* — Viksnins Harris Padys Malen LLP

(57) ABSTRACT

The invention relates to compounds of the formula (VIII) wherein the moieties $R_1$, $R_2$, $R_3$, $R_4$, and $R_5$ are as defined in the specification, and salts thereof, as well as their use, methods of use for them, methods of their synthesis, and the like. The compounds are protein tyrosine kinase inhibitors and can be used in the treatment of various cancer diseases and cancer-associated pain.

16 Claims, 8 Drawing Sheets
(4 of 8 Drawing Sheet(s) Filed in Color)

BENZIMIDAZOLE ANALOGUES AND RELATED METHODS

CROSS-REFERENCE TO RELATED APPLICATIONS

The present invention is a national stage application filed under 35 U.S.C. § 371 of international application PCT/US2015/033962, filed under the authority of the Patent Cooperation Treaty on Jun. 3, 2015, which claims priority to U.S. Provisional Patent Application No. 62/007,321, filed Jun. 3, 2014, the disclosures of which are hereby incorporated by reference.

STATEMENT REGARDING FEDERALLY FUNDED RESEARCH

This invention was made with government support under Grant No. T32 GM008804, awarded by the National Institutes of Health. The Government has certain rights in the invention

BACKGROUND OF THE INVENTION

Protein kinases (PKs) are enzymes which catalyze the phosphorylation of specific serine, threonine, or tyrosine residues in cellular proteins. These post-translational modifications of substrate proteins act as a molecular switch, playing a central role in diverse biological processes such as the control of cell growth, metabolism, tumor microenvironment (such as VEGFR), differentiation, and apoptosis. Aberrant, excessive, or, more generally, inappropriate PK activity has been observed in several disease states including malignant proliferative disorders such as RET gain of function mutations for medullary thyroid cancer (MTC) and other human malignancies, ITD (Internal Tandem Duplication)-mutations in Flt3 for acute myelogenous leukemia (AML), c-Kit mutation for gastrointestinal stromal tumors (GIST), and Bcr-abl rearrangement for chronic myelogenous leukemia (CML). In addition, the activation and/or overexpression of tyrosine kinases such as Trk-A, Trk-B, Trk-C, and RET has been linked to severe pain in cancer patients, especially pancreatic cancer. Many tyrosine kinases are homologous to each other; the inhibition of one tyrosine kinase will also likely produce some inhibitory activity on other tyrosine kinases. For example, imatinib has been used as a therapeutic not only for CML patients (based on the inhibition of Bcr-abl kinase), but also GIST cancer patients (based on the inhibition of c-Kit kinase). The recent advance of basic and clinical studies on the tyrosine kinases has demonstrated that many tyrosine kinases may be targeted by drugs. For example, more than a dozen new drugs targeting VEGFR2, Bcr-abl, Flt3, platelet-derived growth factor receptor (PDGFR), and c-Kit have been approved in the last decade. A few targets and their implications for cancer therapy are briefly described.

RET

In 1985, the RET (Re-arranged during transfection) gene was identified as a novel oncogene activated through DNA rearrangement (Takahashi, M. *Cell,* 1985, 42, 581-588).

MTC (Medullary Thyroid Carcinoma) is a malignancy of the C cells in the thyroid gland. MTC can be either sporadic or familial as part of Multiple Endocrine Neoplasia type 2 syndromes MEN2A and MEN2B. Both familial (about 95%) and sporadic (about 50%) MTC display gain-of-function point mutations in the RET proto-oncogene leading to increased pro-survival signaling and cell growth. RET signaling sustains tumorigenesis. As a result, blocking this RET signaling provides an "Achilles' heel" treatment avenue for MTC patients. Multiple endocrine neoplasia 2B is an inherited syndrome caused primarily by the M918T mutation in the kinase domain of the RET receptor, while multiple endocrine neoplasia 2A is primarily caused by mutation of C634 (Santoro, M. et al *Science,* 1995, 267, 381). Neither mutation is located in the ATP binding site. Isolated familial MTC is caused by different mutations either in RET extracellular or intracellular domains, including the mutations V804M and V804L, which target the gatekeeper residue in the ATP binding site of the kinase. Conventional systemic treatment for MTC has been generally poorly effective, with 56% of patients experiencing post-surgical relapses due to early metastasis (Wells, Jr. S. A. et al, *Clin. Cancer Res.* 2009, 15, 7119-7123).

PTC (Papillary Thyroid Carcinoma) arises from follicular thyroid cells. In PTC, RET is targeted by chromosomal rearrangements that result in the in-frame fusion of part of its intracellular domain with the 5'-end of heterologous genes. About 60,000 new cases of thyroid cancer were estimated in the United States in 2012. Distant metastases are observed at presentation in fewer than 5% of the differentiated thyroid cancer patients, and recurrent disease occurs in 10-15%. Treatment of recurrent disease mainly includes surgery and radioiodine. However, treatment of radioactive refractory PTC disease is still an unmet medical need (Schlumberger, M. *Thyroid,* 2009, 19, 1393-1400).

Lung cancer is the leading cause of cancer-related mortality. Treatment paradigms for non-small-cell lung cancer (NSCLC), which accounts for the majority of all lung cancers, have shifted away from a histologic diagnosis to a diagnosis utilizing molecular subtypes. Some "molecular driver mutations" can result in constitutively active mutant signaling proteins, such as EGFR and ALK. Recently, some studies identified RET kinase fusions (KIF5B-RET and more rarely RET/PTC variants) in about 1% of patients with adenocarcinoma-type NSCLC. As rapidly as four years after the identification of ALK fusions in lung cancer, one ALK inhibitor for NSCLC was approved by FDA. Therefore, RET-positive NSCLC patients may similarly benefit from specific targeted therapies (Hutchinson, K. E. *Nat. Med.* 2012, 18, 349-351).

CMML is a myeloproliferative disorder that presents monocytosis. Myeloproliferative neoplasms are frequently associated with aberrant constitutive tyrosine kinase activity resulting from chimeric fusion genes or point mutations. Two novel fusion genes in CMML, BCR-RET and FGFR10P-RET, have been reported. Blocking activity of RET in CMML is important for reestablishing signaling homeostasis, regenerating proper hematopoietic differentiation, and controlling aberrant tumorigenic signaling (Ballerini, P. et al, *Leukemia* 2012, 1-6).

RET overexpression in a subset of ER-positive breast cancers was also recently identified. In situ hybridization (a technique to determine the presence or absence of genetic sequences in tissue) of a cohort of 245 invasive breast cancers detected RET and GFRα1 mRNA in 29.7% and 59.4% of the tumors, respectively. The majority of these tumors were ER-positive. A similar finding was reported in a survey of breast cancer cell lines. Furthermore, qPCR analysis of a small panel of breast tumor primary cells detected preferential expression of RET mRNA in ER-positive samples. Finally, these studies are strengthened by microarray studies showing that in a set of 36 breast cancer samples, RET expression positively correlated with ER expression. The role of RET in tamoxifen-resistant breast cancer was further validated in the cell-based assay format by Dr. Isacke and her colleagues. In ERα-positive breast cancer cells, activation of the receptor tyrosine kinase RET by its ligand GDNF resulted in increased ERα phosphorylation on Ser118 and Ser167, and estrogen-independent activation of ERα transcriptional activity. In vitro RET downregulation resulted in a 6.2-fold increase in sensitivity of MCF7 cells to the antiproliferative effects of tamoxifen, whereas GDNF stimulation had a protective effect against the drug. In the tamoxifen-resistant MCF7 cells, targeting RET restored tamoxifen sensitivity. Finally, examination of two independent tissue microarrays of primary human breast cancers revealed that expression of RET protein was significantly associated with ERα-positive tumors and that there was a two-fold increase in the number of RET-positive tumors in patients who subsequently developed invasive recurrence after adjuvant tamoxifen treatment (Morandi, A. *Trends in Mol. Med.* 2011, 17, 149-157).

VEGFR

Vascular endothelial growth factor (VEGF) is an important signaling protein involved in both vasculogenesis and angiogenesis. As its name implies, VEGF activity is restricted mainly to cells of the vascular endothelium, although it does have effects on a limited number of other cell types. In vitro, VEGF has been shown to stimulate endothelial cell mitogenesis and cell migration. VEGF also enhances microvascular permeability and is sometimes referred to as vascular permeability factor. VEGFR kinases have been used as a target for solid tumors, such as malignancies that are highly vascular like renal carcinoma, glioblastoma, and liver cancers (Bhargava, P. *Curr Oncol Rep,* 2011, 103-111).

FLT3

While cure rates for acute myeloid leukemia (AML) have improved over the past four decades, survival remains suboptimal. Five-year survival for patients under 60 years old is only 40%. The standard of care for most newly diagnosed patients with AML consists of induction chemotherapy with infusional cytarabine and an anthracycline.

Mutations in the FMS-like tyrosine kinase 3 (FLT3) gene characterize more than 30% of AML cases. FLT3 internal tandem duplication (ITD) mutations, accounting for approximately 23% of AML cases, are associated with a particularly poor prognosis. The prognostic implications of FLT3/D835 point mutations found at diagnosis, comprising approximately 7% of cases, are not yet well established. Inhibiting FLT3 and its mutation would be advantageous.

c-KIT c-Kit is a receptor tyrosine kinase that normally controls the function of primitive hematopoietic cells, melanocytes and germ cells. It has become clear that uncontrolled activity of c-Kit contributes to formation of an array of human tumors. The unregulated activity of c-Kit may be due to overexpression, autocrine loops, or mutational activation. This makes c-Kit an excellent target for cancer therapies in these tumors, especially GIST and AML (Von Mehren, M. *Clin. Colorectal Cancer,* 2006, S30-40).

TRK

Tropomyosin-related kinases (Trks) are receptor tyrosine kinases normally expressed in neuronal tissue where they play important role in both development and function. The Trk receptor family is composed of three members (A, B, and C) activated by specific ligands called neurotrophins. Each Trk receptor contains an extracellular domain, a transmembrane region, and an intracellular domain which upon binding of their respective ligand (nerve growth factor (NGF) for TrkA, brain-derived growth factor (BDNF) and NT-4/5 for TrkB, and NT3 for TrkC), triggers oligomerization of the receptors, phosphorylation of specific tyrosine residues in the kinase domain, and down-stream signal transduction pathways, including survival, proliferation, and differentiation in normal and neoplastic neuronal cells. Deregulation of TrkA and TrkB and their cognate ligands has been described in numerous types of cancers including prostate, breast, colorectal, ovarian, lung, pancreas, melanoma, thyroid, and neuroblastoma, and occurs mainly through wild type receptor overexpression, activation, amplification, and/or mutation. Importantly, increased Trks activation in tumor tissues correlates with an aggressive phenotype and poor clinical outcome. Additionally, Trks, as well as RET, play a role for the perineural invasion and associated cancer pain.

PDGFR

Platelet-derived growth factor acts as a potent mitogen and chemotactic factor for various cells such as fibroblasts, smooth muscle cells, mesenchymal cells, and brain glial cells. Abnormal PDGF-induced cell proliferation has been proposed to lead to proliferative disorders. There is a need for a PDGFR inhibitor that offers therapeutic benefits for proliferative disorders such as gastrointestinal stromal tumors (GIST), glioma, and melanoma.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
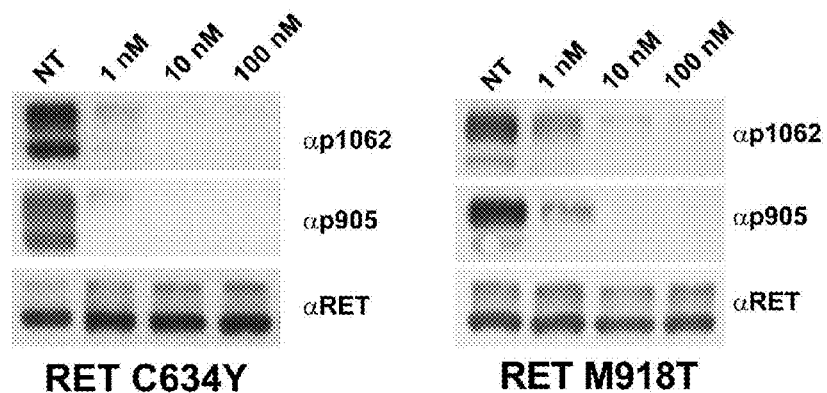
FIG. 1: Photographs of blots showing inhibition of phosphorylation of RET/C634Y and RET/M918T in intact cells by Pz-1 or vehicle (NT: not treated). Serum-starved NIH3T3 cells expressing RET/C634Y or RET/M918T mutants were treated for 2 hr with indicated concentrations of Pz-1. 50 μg of total cell lysates were subjected to immunoblotting with anti-phospho-Y1062 (αp1062) or anti-phospho-Y905 (αp905) RET antibodies. The blots were normalized using anti-RET (αRET) antibodies.

In a first broad aspect, provided herein are compounds of the Formula VIII:

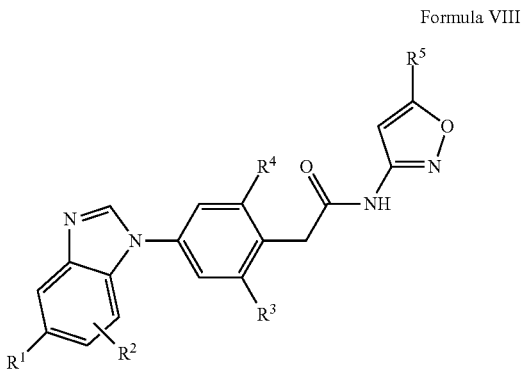

Formula VIII wherein $R^1$ is unsubstituted or substituted (with $R^6$) aryl or heteroaryl; $R^2$ is selected from the group consisting of H, $(C_1-C_3)$alkyl, halo, —CN, —O—$(C_1-C_3)$alkyl, —O—$(CH_2)_n$, X, —N($R^7$)($R^8$), —CONH$(CH_2)_n$, X, —SO$_2$NH$(CH_2)_n$X, and —SO$_2$($C_1-C_3$)alkyl; $R^3$ and $R^4$ are each independently H, $(C_1-C_6)$alkyl, or CN; $R^5$ is —$(C_1-C_3)$alkyl or —$(C_1-C_3)$alkyl substituted with one to three flourines; $R^6$ is H, OH, NH$_2$, $(C_1-C_3)$alkyl, halo, —CN, —O$(C_1-C_3)$alkyl, —O$(CH_2)_n$X, —N($R^7$)($R^8$), —CONH$_2$, —CONH$(CH_2)_n$X, —SO$_2$NH$(CH_2)_n$X, or —SO$_2$($C_1-C_3$)alkyl; X is O$R^9$, N($R^7$)($R^8$); $R^7$ and $R^8$ are each independently hydrogen or $(C_1-C_4)$alkyl or $(C_1-C_4)$alkoxy, and can form a ring between each other; n is 2 or 3; and $R^9$ is H or $(C_1-C_3)$alkyl. Further provided are salts, isomers, steroisomers, enantiomers, racemates, solvates, hydrates, polymorphs, and prodrugs of Formula VIII.

In certain embodiments, the compound of Formula VIII is selected from the group consisting of: N-(5-(tert-butyl)isoxazol-3-yl)-2-(4-(5-(1-methyl-1H-pyrazol-4-yl)-1H-benzo[d]imidazol-1-yl)phenyl)acetamide (Pz-1); 2-(4-(5-(1H-pyrazol-4-yl)-1H-benzo[d]imidazol-1-yl)phenyl)-N-(5-(tert-butyl)isoxazol-3-yl)acetamide; N-(5-(tert-butyl)isoxazol-3-yl)-2-(4-(5-(2,3-dimethylphenyl)-1H-benzo[d]imidazol-1-yl)phenyl)acetamide; N-(5-(tert-butyl)isoxazol-3-yl)-2-(4-(5-(2-fluoropyridin-3-yl)-1H-benzo[d]imidazol-1-yl)phenyl)acetamide; N-(5-(tert-butyl)isoxazol-3-yl)-2-(4-(5-(2,4-dimethoxyphenyl)-1H-benzo[d]imidazol-1-yl)phenyl)acetamide; N-(5-(tert-butyl)isoxazol-3-yl)-2-(4-(5-(thiophen-3-yl)-1H-benzo[d]imidazol-1-yl)phenyl)acetamide; N-(5-(tert-butyl)isoxazol-3-yl)-2-(4-(5-(2,4-difluorophenyl)-1H-benzo[d]imidazol-1-yl)phenyl)acetamide; N-(5-(tert-butyl)isoxazol-3-yl)-2-(4-(5-(2,4-dichlorophenyl)-1H-benzo[d]imidazol-1-yl)phenyl)acetamide; N-(5-(tert-butyl)isoxazol-3-yl)-2-(4-(5-(4-(methylthio)phenyl)-1H-benzo[d]imidazol-1-yl)phenyl)acetamide; N-(5-(tert-butyl)isoxazol-3-yl)-2-(4-(5-(2-methoxyphenyl)-1H-benzo[d]imidazol-1-yl)phenyl)acetamide; N-(5-(tert-butyl)isoxazol-3-yl)-2-(4-(5-(6-fluoropyridin-3-yl)-1H-benzo[d]imidazol-1-yl)phenyl)acetamide; N-(5-(tert-butyl)isoxazol-3-yl)-2-(4-(5-(2-methoxypyridin-3-yl)-1H-benzo[d]imidazol-1-yl)phenyl)acetamide; N-(5-(tert-butyl)isoxazol-3-yl)-2-(4-(5-(pyridin-3-yl)-1H-benzo[d]imidazol-1-yl)phenyl)acetamide; N-(5-(tert-butyl)isoxazol-3-yl)-2-(4-(5-(6-morpholinopyridin-3-yl)-1H-benzo[d]imidazol-1-yl)phenyl)acetamide; N-(5-(tert-butyl)isoxazol-3-yl)-2-(4-(5-(pyridin-4-yl)-1H-benzo[d]imidazol-1-yl)phenyl)acetamide; N-(5-(tert-butyl)isoxazol-3-yl)-2-(4-(5-(4-(methylsulfonyl)phenyl)-1H-benzo[d]imidazol-1-yl)phenyl)acetamide; N-(5-(tert-butyl)isoxazol-3-yl)-2-(4-(5-(pyrimidin-5-yl)-1H-benzo[d]imidazol-1-yl)phenyl)acetamide; N-(5-(tert-butyl)isoxazol-3-yl)-2-(4-(5-(pyridin-2-yl)-1H-benzo[d]imidazol-1-yl)phenyl)acetamide; N-(5-(tert-butyl)isoxazol-3-yl)-2-(4-(5-(6-methylpyridin-2-yl)-1H-benzo[d]imidazol-1-yl)phenyl)acetamide; and N-(5-(tert-butyl)isoxazol-3-yl)-2-(4-(5-phenyl-1H-benzo[d]imidazol-1-yl)phenyl)acetamide.

In a particular embodiment, the compound of Formula VIII is N-(5-(tert-butyl)isoxazol-3-yl)-2-(4-(5-(1-methyl-1H-pyrazol-4-yl)-1H-benzo[d]imidazol-1-yl)phenyl)acetamide (Pz-1).

In a second broad aspect, provided herein are methods of making tyrosine kinase inhibitors. A first method involves reacting a substituted aniline with an activated fluoride compound in a nucleophilic addition reaction to produce an addition product; selectively reducing the addition product to produce a first reduction product; cyclizing the reduced product to produce a cyclized intermediate; coupling the cyclized intermediate with a boronic acid or tin derivative to produce an ester; and reducing the ester to produce a second reduction product; and aminating the second reduction produce to produce a tyrosine kinase inhibitor.

In certain embodiments, the substituted aniline comprises a bromine at the para position. In certain embodiments, the selective reduction comprises reducing an NO$_2$ group to NH$_2$ while not reducing bromine. In certain embodiments, the cyclization comprises activating the reduced product with an acid. In particular embodiments, the acid comprises pTSA. In certain embodiments, the cyclized intermediate comprises ethyl 2-(4-(5-bromo-1H-benzo[d]imidazol-1-yl)phenyl)acetate.

In certain embodiments, the coupling is palladium-catalyzed. In certain embodiments, bromine is a leaving group in the coupling step. In certain embodiments, the coupling step comprises Suzuki coupling. In certain embodiments, the ester is selected from the group consisting of: ethyl 2-(4-(5-(1H-pyrazol-4-yl)-1H-benzo[d]imidazol-1-yl)phenyl)acetate; ethyl 2-(4-(5-(2,3-dimethylphenyl)-1H-benzo[d]imidazol-1-yl)phenyl)acetate; ethyl 2-(4-(5-(2-fluoropyridin-3-yl)-1H-benzo[d]imidazol-1-yl)phenyl)acetate; ethyl 2-(4-(5-(2,4-dimethoxyphenyl)-1H-benzo[d]imidazol-1-yl)phenyl)acetate; ethyl 2-(4-(5-(thiophen-3-yl)-1H-benzo[d]imidazol-1-yl)phenyl)acetate; ethyl 2-(4-(5-(2,4-difluorophenyl)-1H-benzo[d]imidazol-1-yl)phenyl)acetate; ethyl 2-(4-(5-(2,4-dichlorophenyl)-1H-benzo[d]imidazol-1-yl)phenyl)acetate; ethyl 2-(4-(5-(4-(methylthio)phenyl)-1H-benzo[d]imidazol-1-yl)phenyl)acetate; ethyl 2-(4-(5-(2-methoxyphenyl)-1H-benzo[d]imidazol-1-yl)phenyl)acetate; ethyl 2-(4-(5-(6-fluoropyridin-3-yl)-1H-benzo[d]imidazol-1-yl)phenyl)acetate; ethyl 2-(4-(5-(2-methoxypyridin-3-yl)-1H-benzo[d]imidazol-1-yl)phenyl)acetate; ethyl 2(4-(5-(pyridin-3-yl)-1H-benzo[d]imidazol-1-yl)phenyl)acetate; ethyl 2-(4-(5-(6-morpholinopyridin-3-yl)-1H-benzo[d]imidazol-1-yl)phenyl)acetate; ethyl 2-(4-(5-(pyridin-4-yl)-1H-benzo[d]imidazol-1-yl)phenyl)acetate; ethyl 2-(4-(5-(4-(methylsulfonyl)phenyl)-1H-benzo[d]imidazol-1-yl)phenyl)acetate; ethyl 2-(4-(5-(pyrimidin-5-yl)-1H-benzo[d]imidazol-1-yl)phenyl)acetate; ethyl 2-(4-(5-(pyridin-2-yl)-1H-benzo[d]imidazol-1-yl)phenyl)acetate; ethyl 2-(4-(5-(6- methylpyridin-2-yl)-1H-benzo[d]imidazol-1-yl)phenyl) acetate; and ethyl 2(4-(5-phenyl-1H-benzo[d]imidazol-1-yl)phenyl)acetate. In certain embodiments, the ester consists essentially of ethyl 2-(4-(5-(1-methyl-1H-pyrazol-4-yl)-1H-benzo[d]imidazol-1-yl)phenyl)acetate.

In certain embodiments, the second reduction product comprises a compound selected from the group consisting of: lithium 2-(4-(5-(1H-pyrazol-4-yl)-1H-benzo[d]imidazol-1-yl)phenyl)acetate; lithium 2-(4-(5-(2,3-dimethylphenyl)-1H-benzo[d]imidazol-1-yl)phenyl)acetate; lithium 2-(4-(5-(2-fluoropyridin-3-yl)-1H-benzo[d]imidazol-1-yl)phenyl) acetate; lithium 2-(4-(5-(2,4-dimethoxyphenyl)-1H-benzo[d]imidazol-1-yl)phenyl)acetate; lithium 2-(4-(5-(thiophen-3-yl)-1H-benzo[d]imidazol-1-yl)phenyl)acetate; lithium 2-(4-(5-(2,4-difluorophenyl)-1H-benzo[d]imidazol-1-yl) phenyl)acetate; lithium 2-(4-(5-(2,4-dichlorophenyl)-1H-benzo[d]imidazol-1-yl)phenyl)acetate; lithium 2-(4-(5-(4-(methylthio)phenyl)-1H-benzo[d]imidazol-1-yl)phenyl) acetate; lithium 2-(4-(5-(2-methoxyphenyl)-1H-benzo[d]imidazol-1-yl)phenyl)acetate; lithium 2-(4-(5-(6-fluoropyridin-3-yl)-1H-benzo[d]imidazol-1-yl)phenyl) acetate; lithium 2-(4-(5-(2-methoxypyridin-3-yl)-1H-benzo[d]imidazol-1-yl)phenyl)acetate; lithium 2(4-(5-(pyridin-3-yl)-1H-benzo[d]imidazol-1-yl)phenyl)acetate; lithium 2-(4-(5-(6-morpholinopyridin-3-yl)-1H-benzo[d]imidazol-1-yl) phenyl)acetate; lithium 2-(4-(5-(pyridin-4-yl)-1H-benzo[d]imidazol-1-yl)phenyl)acetate; lithium 2-(methylsulfonyl)phenyl)-1H-benzo[d]imidazol-1-yl)phenyl)acetate; lithium 2-(4-(5-(pyrimidin-5-yl)-1H-benzo[d]imidazol-1-yl)phenyl) acetate; lithium 2-(4-(5-(pyridin-2-yl)-1H-benzo[d]imidazol-1-yl)phenyl)acetate; lithium 2-(4-(5-(6-methylpyridin-2-yl)-1H-benzo[d]imidazol-1-yl)phenyl)acetate; and lithium 2-(4-(5-phenyl-1H-benzo[d]imidazol-1-yl)phenyl)acetate.

In certain embodiments, the second reduction product consists essentially of lithium 2-(4-(5-(1-methyl-1H-pyrazol-4-yl)-1H-benzo[d]imidazol-1-yl)phenyl)acetate.

A second method involves reacting a boronic ester with a halo-aryl or heteroaryl in the presence of a catalyst and a base to produce an intermediate; coupling the intermediate with a boronic acid or tin derivative to produce a tyrosine kinase inhibitor precursor; and reducing and aminating the tyrosine kinase inhibitor precursor to produce a tyrosine kinase inhibitor. In certain embodiments, the base comprises potassium acetate.

In certain embodiments, the halo-aryl or heteroaryl comprises pyrrolyl, pyrazolyl, pyranyl, thiopyranyl, furanyl, imidazolyl, pyridyl, thiazolyl, triazinyl, phthalimidyl, indolyl, purinyl, benzothiazolyl, or combinations thereof. In certain embodiments, the halo-aryl or heteroaryl comprises a heterocyclical radical selected from the group consisting of oxiranyl, azirinyl, aziridinyl, 1,2-oxathiolanyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, (S-oxo or S,S-dioxo)-thiomorpholinyl, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, benzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl, and chromanyl.

In certain embodiments, the intermediate comprises ethyl 2-(4-(5-(4,4,5,5-tetramethyl-1,3,2-dioxaborolan-2-yl)-1H-benzo[d]imidazol-1-yl)phenyl)acetate.

In certain embodiments, the tyrosine kinase inhibitor precursor is selected from the group consisting of: ethyl 2-(4-(5-(1H-pyrazol-4-yl)-1H-benzo[d]imidazol-1-yl)phenyl)acetate; ethyl 2-(4-(5-(2,3-dimethylphenyl)-1H-benzo[d]imidazol-1-yl)phenyl)acetate; ethyl 2-(4-(5-(2-fluoropyridin-3-yl)-1H-benzo[d]imidazol-1-yl)phenyl)acetate; ethyl 2-(4-(5-(2,4-dimethoxyphenyl)-1H-benzo[d]imidazol-1-yl)phenyl)acetate; ethyl 2-(4-(5-(thiophen-3-yl)-1H-benzo[d]imidazol-1-yl)phenyl)acetate; ethyl 2-(4-(5-(2,4-difluorophenyl)-1H-benzo[d]imidazol-1-yl)phenyl)acetate; ethyl 2-(4-(5-(2,4-dichlorophenyl)-1H-benzo[d]imidazol-1-yl)phenyl)acetate; ethyl 2-(4-(5-(4-(methylthio)phenyl)-1H-benzo[d]imidazol-1-yl)phenyl)acetate; ethyl 2-(4-(5-(2-methoxyphenyl)-1H-benzo[d]imidazol-1-yl)phenyl)acetate; ethyl 2-(4-(5-(6-fluoropyridin-3-yl)-1H-benzo[d]imidazol-1-yl)phenyl)acetate; ethyl 2-(4-(5-(2-methoxypyridin-3-yl)-1H-benzo[d]imidazol-1-yl)phenyl)acetate; ethyl 2-(4-(5-(pyridin-3-yl)-1H-benzo[d]imidazol-1-yl)phenyl)acetate; ethyl 2-(4-(5-(6-morpholinopyridin-3-yl)-1H-benzo[d]imidazol-1-yl)phenyl)acetate; ethyl 2-(4-(5-(pyridin-4-yl)-1H-benzo[d]imidazol-1-yl)phenyl)acetate; ethyl 2-(4-(5-(4-(methylsulfonyl)phenyl)-1H-benzo[d]imidazol-1-yl) phenyl)acetate; ethyl 2-(4-(5-(pyrimidin-5-yl)-1H-benzo[d]imidazol-1-yl)phenyl)acetate; ethyl 2-(4-(5-(pyridin-2-yl)-1H-benzo[d]imidazol-1-yl)phenyl)acetate; ethyl 2-(4-(5-(6-methylpyridin-2-yl)-1H-benzo[d]imidazol-1-yl)phenyl) acetate; and ethyl 2-(4-(5-phenyl-1H-benzo[d]imidazol-1-yl)phenyl)acetate. In certain embodiments, the tyrosine kinase inhibitor precursor consists essentially of ethyl 2-(4-(5-methyl-1H-pyrazol-4-yl)-1H-benzo[d]imidazol-1-yl)phenyl)acetate.

In certain embodiments, the tyrosine kinase inhibitor precursor is reduced to a reduction product comprising a compound selected from the group consisting of: lithium 2-(4-(5-(1H-pyrazol-4-yl)-1H-benzo[d]imidazol-1-yl)phenyl)acetate; lithium 2(4-(5-(2,3-dimethylphenyl)-1H-benzo[d]imidazol-1-yl(phenyl)acetate; lithium 2-(4-(5-(2-fluoropyridin-3-yl)-1H-benzo[d]imidazol-1-yl)phenyl)acetate; lithium 2-(4-(5-(2,4-dimethoxyphenyl)-1H-benzo[d]imidazol-1-yl)phenyl)acetate; lithium 2-(4-(5-(thiophen-3-yl)-1H-benzo[d]imidazol-1-yl)phenyl)acetate; lithium 2-(4-(5-(2,4-difluorophenyl)-1H-benzo[d]imidazol-1-yl)phenyl) acetate; lithium 2-(4-(5-(2,4-dichlorophenyl)-1H-benzo[d]imidazol-1-yl)phenyl)acetate; lithium 2-(4-(5-(4-(methylthio)phenyl)-1H-benzo[d]imidazol-1-yl)phenyl) acetate; lithium 2-(4-(5methoxyphenyl)-1H-benzo[d]imidazol-1-yl)phenyl)acetate; lithium 2-(4-(5-(6-fluoropyridin-3-yl)-1H-benzo[d]imidazol-1-yl)phenyl) acetate; lithium 2-(4-(5-(2-methoxypyridin-3-yl)-1H-benzo[d]imidazol-1-yl)phenyl)acetate; lithium 2-(4-(5-(pyridin-3-yl)-1H-benzo[d]imidazol-1-yl)phenyl)acetate; lithium 2-(4-(5-(6-morpholinopyridin-3-yl)-1H-benzo[d]imidazol-1-yl) phenyl)acetate; lithium 2-(4-(5-(pyridin-4-yl)-1H-benzo[d]imidazol-1-yl)phenyl)acetate; lithium 2-(4-(5-(4-(methylsulfonyl)phenyl)-1H-benzo[d]imidazol-1-yl) phenyl)acetate; lithium 2-(4-(5-(pyrimidin-5-yl)-1H-benzo[d]imidazol-1-yl)phenyl)acetate; lithium 2-(4-(5-(pyridin-2-yl)-1H-benzo[d]imidazol-1-yl)phenyl)acetate; lithium 2-(4-(5-(6-methylpyridin-2-yl)-1H-benzo[d]imidazol-1-yl) phenyl)acetate; and lithium 2(4-(5-phenyl-1H-benzo[d]imidazol-1-yl)phenyl)acetate. In certain embodiments, the tyrosine kinase inhibitor precursor is reduced to a reduction product consisting essentially of 2-(4-(5-(1-methyl-1H-pyrazol-4-yl)-1H-benzo[d]imidazol-1-yl)phenyl)acetate.

In another broad aspect, provided herein is a pharmaceutical composition. The pharmaceutical composition comprises a compound of Formula VIII and a pharmaceutically acceptable carrier, diluent, or excipient.

Further provided are methods of treating a subject with cancer, inhibiting phosphorylation, and inhibiting proliferation of cells including thyroid cancer cells. In certain embodiments, the methods comprise administering an effective amount of a compound of Formula VIII to a subject or cells. In certain embodiments, the compound comprises N-(5-(tert-butyl)isoxazol-3-yl)-2-(4-(5-(1-methyl-1H-pyrazol-4-yl)-1H-benzo[d]imidazol-1-yl)phenyl)acetamide (Pz-1). In certain embodiments, the thyroid cancer cells comprise MTC.

Further provided is a method of inhibiting a tyrosine kinase, comprising treating cells with an effective amount of a compound of Formula VIII. In certain embodiments, the tyrosine kinase in selected from the group consisting of RET, FLT3, c-Kit, VEGFR, Trk-A, Trk-B, Trk-C, and PDGFR. In certain embodiments, the compound exhibits kinase domain with an $IC_{50}$ value of less than 1 μM.

Further provided is a method of treating cancer-associated pain. The method involves administering an effective amount of a pharmaceutical composition comprising a compound of Formula VIII and a pharmaceutically acceptable carrier, diluent, or excipient to a patient in need thereof.

Further provided are kits. In a first embodiment, a kit for the preparation of a tyrosine kinase inhibitor comprises a first container housing a substitute aniline, and a second container housing an activated fluoride compound. In certain embodiments, the kit further comprises one or more reducing agents, a boronic acid, or a tin derivative. In a second embodiment, a kit for the preparation of a tyrosine kinase inhibitor includes a first container housing a boronic ester, a second container housing a halo-aryl or heteroaryl, and a catalyst. In certain embodiments, the kit further comprises one or more reducing agents. In a third embodiment, a kit for the preparation of a pharmaceutical composition comprises a first container housing a compound of Formula VIII, and a second container housing a pharmaceutically acceptable carrier, diluent, or excipient.

DETAILED DESCRIPTION

Various embodiments are described in the present disclosure in the context of compounds, methods of making compounds, and methods of using compounds. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" in this disclosure indicates that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

Definitions

The general chemical terms used herein have their usual meanings in the art. For example, as used herein, the term "$C_1$-$C_4$ alkyl," alone or in combination, denotes a straight-chain or branched-chain $C_1$-$C_4$ alkyl group consisting of carbon and hydrogen atoms, examples of which are methyl, ethyl, propyl, isopropyl, butyl, sec-butyl, tert-butyl, and the like.

As used herein, the term "halo" or "halogen" represents fluorine, chlorine, bromine, or iodine. As used herein, the term "$C_1$-$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$-$C_6$ alkyl" includes within its definition the terms "$C_1$-$C_4$ alkyl" and "$C_1$-$C_3$ alkyl." The term "carboxy" or "carboxyl" refers to a carboxylic acid. The term "carboxamide" refers to a carbonyl substituted with an $NH_2$ moiety. The term "oxo" refers to a carbonyl group.

As used herein, the term "heteroaryl" means an aryl moiety which contains 1-5 heteroatoms selected from O, S, and N. Examples of heteroaryl groups include pyrrolyl, pyrazolyl, pyranyl, thiopyranyl, furanyl, imidazolyl, pyridyl, thiazolyl, triazinyl, phthalimidyl, indolyl, purinyl, and benzothiazolyl. Heteroaryl is especially a heterocyclyl radical selected from the group consisting of oxiranyl, azirinyl, aziridinyl, 1,2-oxathiolanyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, (S-oxo or S,S-dioxo)-thiomorpholinyl, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl and chromanyl.

Various abbreviations are used herein. The term DCM refers to dichloromethene. The term DIPEA refers to N,N-Diisopropylthylamne. The term $Pd_2(dba)_3$ refers to tris(dibenzylideneacetone)dipalladium. The term dppf refers to 1,1'-bis(diphenylphosphino) ferrocene. The term DMA refers to N,N-dimethylacetamide. The term DMF refers to N,N-dimethylformamide. The term DMSO refers to dimethylsulfoxide. The term EDC refers to 1-ethyl-3-(3-dimethylaminopropyl)carbodiimide. The term EtOAc refers to ethyl acetate. The term EtOH refers to ethyl alcohol. The term ES refers to electron spray. The term h refers to hour(s). The term HOAc refers to acetic acid. The term HOAt refers to 1-hydroxy-7-azabenzotriazole. The term IPA refers to isopropyl alcohol. The term KOAc refers to potassium acetate. The term LC refers to liquid chromatography. The term LiOH refers to lithium hydroxide. The term $MgSO_4$ refers to magnesium sulfate. The term min refers to minutes. The term mL refers to milliliter. The term mmol refers to millimole. The term MS refers to mass spectrum. The term $NaHCO_3$ refers to sodium bicarbonate. The term pTSA refers to p-toluenesulfonic acid. The term $P(CY)_3$ refers to tricyclohexylphosphine. The term RT refers to room temperature. The term THF refers to tetrahydrofuran. The term TLC refers to thin layer chromatography. The term TMOF refers to trimethyl orthoformate.

Where the plural form is used for compounds, salts, pharmaceutical preparations, diseases, disorders, and the like, it is intended to mean also a single compound, salt, pharmaceutical preparation, disease, or the like. Where "a" or "an" is used, it refers to the indefinite article, or preferably to "one."

General Description

Provided herein are compounds of the Formula VIII:

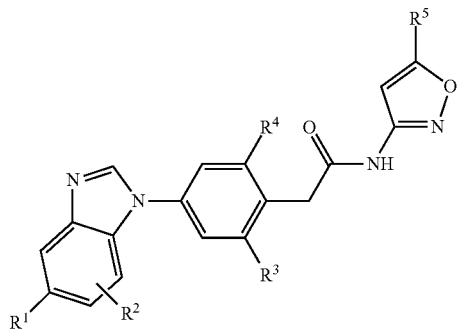

Formula VIII wherein $R^1$ is unsubstituted or substituted (with $R^6$) aryl or heteroaryl; $R^2$ is selected from the group consisting of H, $(C_1\text{-}C_3)$alkyl, halo, —CN, —O—$(C_1\text{-}C_3)$alkyl, —O—$(CH_2)_n X$, —N$(R^7)(R^8)$, —CONH$(CH_2)_n X$, —SO$_2$NH$(CH_2)_n X$, and —SO$_2(C_1\text{-}C_3)$alkyl; $R^3$ and $R^4$ are each independently H, $(C_1\text{-}C_6)$alkyl, or CN; $R^5$ is —$(C_1\text{-}C_4)$ unsubstituted alkyl or $(C_1\text{-}C_3)$ alkyl substituted with one to three fluorines; $R^6$ is H, OH, NH$_2$, $(C_1\text{-}C_3)$alkyl, halo, —CN, —O$(C_1\text{-}C_3)$alkyl, —O$(CH_2)_n X$, —N$(R^7)(R^8)$, —CONH$_2$, —CONH$(CH_2)_n X$, —SO$_2$NH$(CH_2)_n X$, or —SO$_2(C_1\text{-}C_3)$alkyl; X is O$R^9$, N$(R^7)(R^8)$; $R^7$ and $R^8$ are each independently hydrogen or $(C_1\text{-}C_4)$alkyl or $(C_1\text{-}C_4)$alkoxy, and can form a ring between each other; n is 2 or 3; and $R^9$ is H or $(C_1\text{-}C_3)$alkyl; and salts, isomers, stereoisomers, enantiomers, racemates, solvates, hydrates, polymorphs, and prodrugs thereof. Metabolic precursors of compounds of Formula VIII, such as esters or amides, are further provided herein.

By way of non-limiting example, the compounds of Formula VIII specifically include, but are not limited to, the compounds listed below:

1) N-(5-(tert-butyl)isoxazol-3-yl)-2-(4-(5-(1-methyl-1H-pyrazol-4-yl)-1H-benzo[d]imidazol-1-yl)phenyl)acetamide;
2) 2-(4-(5-(1H-pyrazol-4-yl)-1H-benzo[d]imidazol-1-yl)phenyl)-N-(5-(tert-butyl)isoxazol-3-yl)acetamide;
3) N-(5-(tert-butyl)isoxazol-3-yl)-2-(4-(5-(2,3-dimethylphenyl)-1H-benzo[d]imidazol-1-yl)phenyl)acetamide;
4) N-(5-(tert-butyl)isoxazol-3-yl)-2-(4-(5-(2-fluoropyridin-3-yl)-1H-benzo[d]imidazol-1-yl)phenyl)acetamide;
5) N-(5-(tert-butyl)isoxazol-3-yl)-2-(4-(5-(2,4-dimethoxyphenyl)-1H-benzo[d]imidazol-1-yl)phenyl)acetamide;
6) N-(5-(tert-butyl)isoxazol-3-yl)-2-(4-(5-(thiophen-3-yl)-1H-benzo[d]imidazol-1-yl)phenyl)acetamide;
7) N-(5-(tert-butyl)isoxazol-3-yl)-2-(4-(5-(2,4-difluorophenyl)-1H-benzo[d]imidazol-1-yl)phenyl)acetamide; yl)phenyl)acetamide;
8) N-(5-(tert-butyl)isoxazol-3-yl)-2-(4-(5-(2,4-dichlorophenyl)-1H-benzo[d]imidazol-1-yl)phenyl)acetamide;
9) N-(5-(tert-butyl)isoxazol-3-yl)-2-(4-(5-(4-(methylthio)phenyl)-1H-benzo[d]imidazol-1-yl)phenyl)acetamide;
10) N-(5-(tert-butyl)isoxazol-3-yl)-2-(4-(5-(2-methoxyphenyl)-1H-benzo[d]imidazol-1-yl)phenyl)acetamide;
11) N-(5-(tert-butyl)isoxazol-3-yl)-2-(4-(5-(6-fluoropyridin-3-yl)-1H-benzo[d]imidazol-1-yl)phenyl)acetamide;
12) N-(5-(tert-butyl)isoxazol-3-yl)-2-(4-(5-(2-methoxypyridin-3-yl)-1H-benzo[d]imidazol-1-yl)phenyl)acetamide;
13) N-(5-(tert-butyl)isoxazol-3-yl)-2-(4-(5-(pyridin-3-yl)-1H-benzo[d]imidazol-1-yl)phenyl)acetamide;
14) N-(5-(tert-butyl)isoxazol-3-yl)-2-(4-(5-(6-morpholinopyridin-3-yl)-1H-benzo[d]imidazol-1-yl)phenyl)acetamide;
15) N-(5-(tert-butyl)isoxazol-3-yl)-2-(4-(5-(pyridin-4-yl)-1H-benzo[d]imidazol-1-yl)phenyl)acetamide;
16) N-(5-(tert-butyl)isoxazol-3-yl)-2-(4-(5-(4-(methylsulfonyl)phenyl)-1H-benzo[d]imidazol-1-yl)phenyl)acetamide;
17) N-(5-(tert-butyl)isoxazol-3-yl)-2-(4-(5-(pyrimidin-5-yl)-1H-benzo[d]imidazol-1-yl)phenyl)acetamide;
18) N-(5-(tert-butyl)isoxazol-3-yl)-2-(4-(5-(pyridin-2-yl)-1H-benzo[d]imidazol-1-yl)phenyl)acetamide;
19) N-(5-(tert-butyl)isoxazol-3-yl)-2-(4-(5-(6-methylpyridin-2-yl)-1H-benzo[d]imidazol-1-yl)phenyl)acetamide;
20) N-(5-(tert-butyl)isoxazol-3-yl)-2-(4-(5-phenyl-1H-benzo[d]imidazol-1-yl)phenyl)acetamide;

and pharmaceutically acceptable salts thereof. It should be understood that the number preceding the compound name in the above list may be used herein to identify the particular compound to which it corresponds. It is to be further understood that the compounds exemplified in the above list are merely representative of the invention and are not limiting in any fashion. Any of the compounds of the present disclosure are useful as tyrosine kinase inhibitors.

Throughout the specification, compound 1, an example of a compound of Formula VIII, may be referred to as compound 1, N-(5-(tert-butyl)isoxazol-3-yl)-2-(4-(5-(1-methyl-1H-pyrazol-4-yl)-1H-benzo[d]imidazol-1-yl)phenyl)acetamide, Pz-1, Pz-01, or any combination of these terms.

The skilled practitioner will recognize that any of the compounds described herein are capable of forming salts. By way of non-limiting example, the compounds described react with any number of organic or inorganic acids to form pharmaceutically acceptable acid addition salts.

Method of Making

In certain embodiments, the compounds disclosed herein can be made according to the following schemes and examples. It should be understood that many other methods of making the compounds are possible. For example, the skilled artisan will appreciate that the introduction of certain substituents will create asymmetry in the compounds of Formula VIII. The present invention contemplates all enantiomers and mixtures of enantiomers, including racemates. It is preferred that the compounds of the invention containing chiral centers be single enantiomers, but it is not required.

The compounds of the present disclosure can be prepared by a variety of procedures, some of which are illustrated in the schemes depicted below. It will be recognized by one of skill in the art that the individual steps in the following schemes may be varied to provide the compounds of Formula VIII. The particular order of steps required to produce the compounds of Formula VIII is dependent upon the particular compound being synthesized, the starting compound(s), and the relative lability of the substituted moieties.

In certain embodiments, the compounds of Formula VIII are synthesized through Scheme I, which is depicted below.

SCHEME I

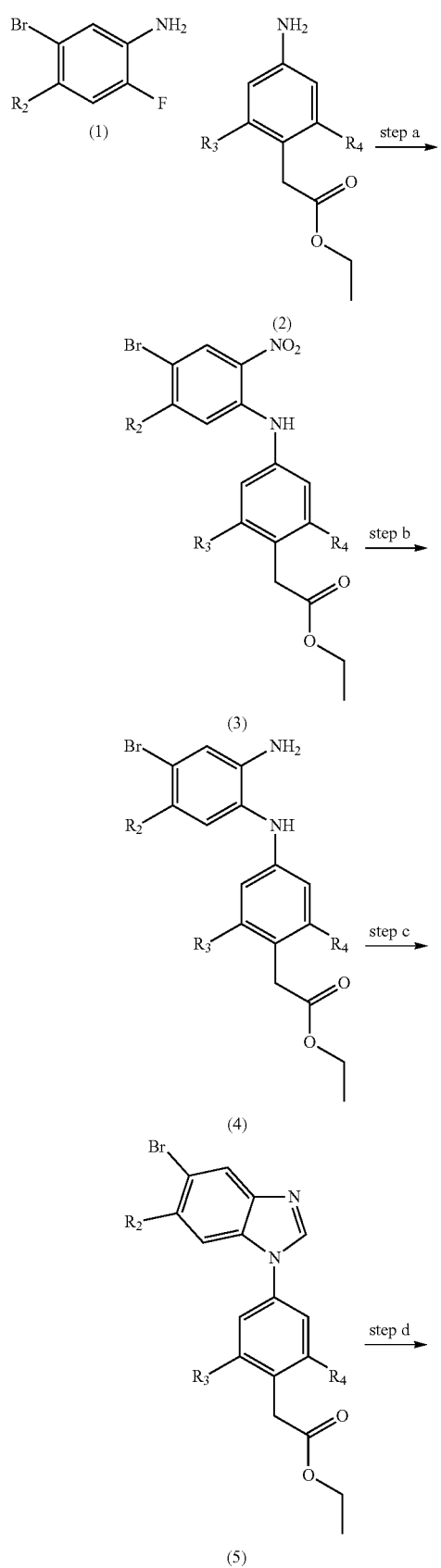

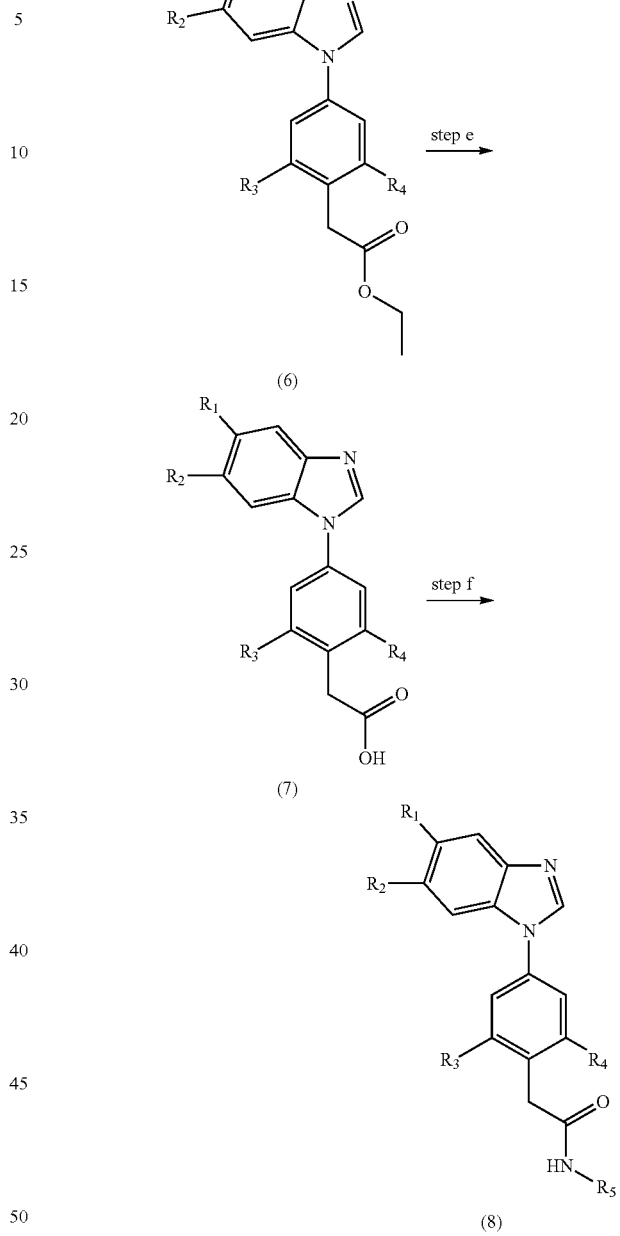

Step a of Scheme I depicts a nucleophilic addition reaction of an appropriately substituted aniline (2) to an activated fluoride compound (1). The para-bromine substitution is important for this reaction; it not only accelerates the replacement of fluorine with $NH_2$, but the bromine atom can also allow the carbon-carbon bond formation through a Suzuki reaction in the resulting intermediate (5). The product can be isolated and purified by techniques known in the art, such as precipitation, filtration, extraction, evaporation, chromatography, and re-crystallization.

In step b of Scheme I, certain conditions are applied to an intermediate 3 to give intermediate 4. Typically, the reaction is carried out in a suitable solvent such as MeOH, EtOH, or acid to selectively reduce the $NO_2$ group to $NH_2$ without the reduction of bromine, but other methods are possible. The reaction is carried out at a temperature ranging from lower than room temperature (such as in an ice bath) to ambient for 4 to 8 h. The product can be isolated and purified by the techniques described above.

Step c of Scheme 1 depicts the cyclization of intermediate 4 to give an optionally substituted intermediate 5. Typically, the appropriate intermediate 4 is activated with a suitable acid, preferably pTSA, in a suitable solvent or in neat TMOF at temperatures of 100° C. and above. The products can be isolated and purified by the techniques described above.

Step d of Scheme I depicts the palladium-catalyzed coupling of intermediate 5 with a boronic acid or tin derivative to give intermediate 6. Typically, the halide, especially bromine, of intermediate 5 is used as a leaving group in the combination of boronic acid or tin analogues in the presence of a suitable catalyst, preferably $Pd_2(dba)_3$, and a suitable base, such as potassium acetate, to further synthesize compounds of Formula VIII (Suzuki reaction: see, e.g. Miyaura, N. et al *Synth. Commun.*, 1981, 513-518).

In certain embodiments, the compounds of Formula VIII can be synthesized through Scheme II, depicted below.

SCHEME II

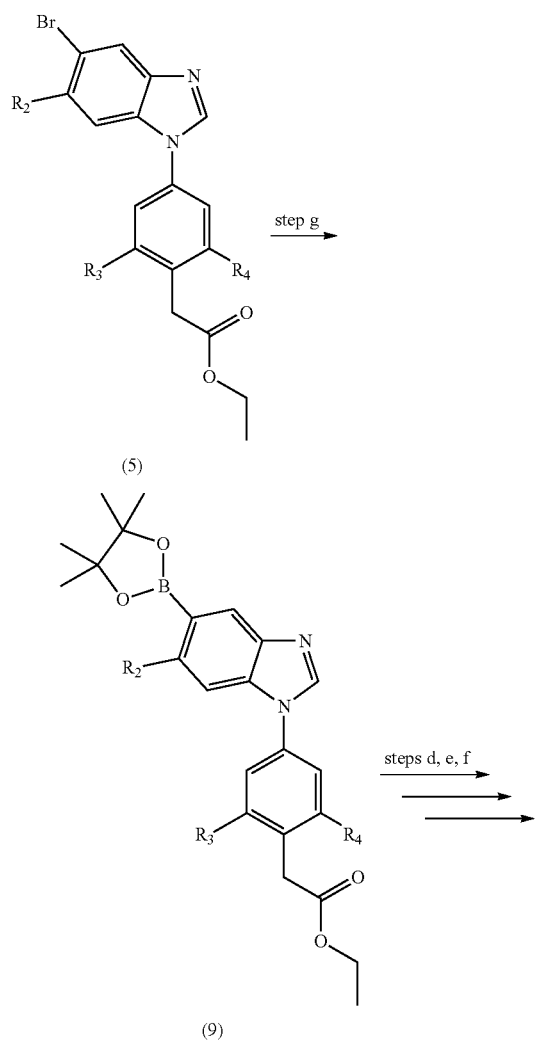

-continued

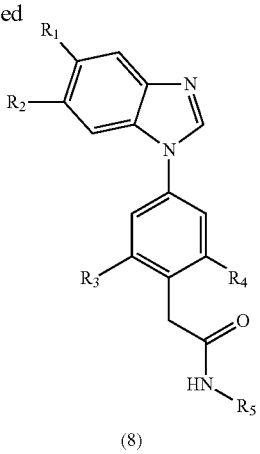

Step e of Scheme II depicts the synthesis of the boronic ester of intermediate 9 by methods known in the art (Li et al, *J. Org. Chem.*, 2002, 5394-5397). In the same way of step d, a halo-aryl or heteroaryl can react with intermediate 9, in the presence of a suitable catalyst, such as $Pd_2(dba)_3$, and a suitable base, such as potassium acetate, to further synthesize compounds of Formula VIII (Suzuki reaction: see, e.g. Miyaura, N. et al *Synth. Commun.*, 1981, 513-518). Compounds 17-20, the IUPAC names of which were given in the list above, can be synthesized via Scheme II, using the same two remaining steps as in Scheme I—steps e and f.

Pharmaceutical Compositions

The compounds of the present disclosure can be incorporated into pharmaceutical compositions for use in the treatment of various diseases. In certain embodiments, salts of Formula VIII are especially useful in pharmaceutical compositions.

A pharmaceutical composition as described herein may be formulated with any of the compounds of Formula VIII, which are tyrosine kinase inhibitors, plus any common excipients, diluents, or carriers. The compositions can be compressed into tablets, or formulated as elixirs or solutions for convenient oral administration or administration by intramuscular or intravenous routes. The compounds can be administered transdermally and may be formulated as sustained release dosage forms and the like.

The compounds, compositions, and formulations provided herein are useful for treating animals, such as humans, for various diseases. A method of treating a human patient according to the present disclosure includes the administration of an effective amount of a tyrosine kinase inhibitor or pharmaceutical composition comprising a tyrosine kinase inhibitor. The tyrosine kinase inhibitors can be formulated into compositions which may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to about 50 mg in the case of parenteral or inhalation administration, and from about 25 to about 500 mg in the case of oral or rectal administration) the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in light of all the relevant circumstances including the condition to be treated, the choice of compound to be administered, and the choice of route of administration. Therefore, the dosage ranges discussed herein are not intended to limit the scope of the present invention in any way.

The formulations useful for separate administration of the tyrosine kinase inhibitors normally contain at least one compound selected from the compounds of Formula VIII (which may be referred to herein as the active ingredient or active substance) mixed with a carrier, or diluted by a carrier, or enclosed or encapsulated by an ingestible carrier in the form of a capsule, sachet, cachet, paper, or other container, or by a disposable container such as an ampoule. A carrier or diluent may be a solid, semi-solid or liquid material which serves as a vehicle, excipient, or medium for the active therapeutic substance. Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol, and propellants such as trichloromonofluoromethane, dichlorodifluoromethane, and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium, or calcium stearates, talc, or mineral oil.

In certain embodiments, pharmaceutical compositions of the present disclosure comprise an effective amount of a compound of Formula VIII and/or additional agents, dissolved or dispersed in a pharmaceutically acceptable carrier. The phrases "pharmaceutical" or "pharmacologically acceptable" refers to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it will be understood that preparations should meet sterility, pyrogenicity, and general safety and purity standards as required by FDA Office of Biological Standards.

A composition disclosed herein may comprise different types of carriers depending on whether it is to be administered in solid, liquid or aerosol form, and whether it needs to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The compounds of the present disclosure are generally effective over a wide dosage range. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hardor soft-shell gelatin capsules, or they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, a polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, such as, but not limited to, sugars or sodium chloride. Prolonged absorption of the injectable compositions can be brought about by the use in the compositions of agents delaying absorption such as, for example, aluminum monostearate, or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. Sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays have been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

Preferred pharmaceutical forms of the present invention are capsules, tablets, suppositories, injectable solutions, creams, and ointments. Especially preferred are formulations for inhalation, such as an aerosol, for injection, and for oral ingestion.

Kits

It is further intended the compounds or compositions disclosed herein could be packaged in the form of a kit containing multiple containers. Many embodiments of such kits are possible. In certain embodiments, a kit comprises multiple components for a process of making a tyrosine kinase inhibitor compound. In particular embodiments, a kit comprises a substituted aniline, an activated fluoride compound, one or more reducing agents, and a boronic acid or tin derivative. In other embodiments, a kit comprises a boronic ester, a halo-aryl or heteroaryl, a catalyst, and optionally, one or more reducing agents. In other embodiments, a kit for preparing a pharmaceutical composition comprises a tyrosine kinase inhibitor, such as a compound of Formula VIII, and a pharmaceutically acceptable carrier, diluent, or excipient. Many other variations and embodiments of kits are envisioned.

The kits typically further include instructions for using the components of the kit to practice the subject methods, but do not need to include such instructions. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a CD-ROM, diskette, or flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example 1. Preparation 1—Preparation of Formula III

Ethyl 4-aminophenyl acetate (3.67 g, 20.45 mmol) was added to a 20 mL microwave vial along with 4-bromo-1-fluoro-2-nitrobenzene (3.00 g, 13.64 mmol) and DMA (10 mL). The reaction mixture was sealed and placed under microwave irradiation for 30 minutes at 160° C. Water was added to the crude reaction mixture and the product was extracted with EtOAc. The organic extract was washed with brine 1×, acidified water (pH ~4) 2×, and brine 2×. The organic layer was collected then dried with $MgSO_4$. The concentrated crude was purified using flash chromatography with hexanes/EtOAc to afford ethyl 2-(4-((4-bromo-2-nitrophenyl)amino)phenyl)acetate 3 as a blood-red oil (4.2 g, 81%). ESMS m/z 379 (M+H)$^+$. The structure of ethyl 2-(4-((4-bromo-2-nitrophenyl)amino)phenyl)acetate (Formula III) is depicted below:

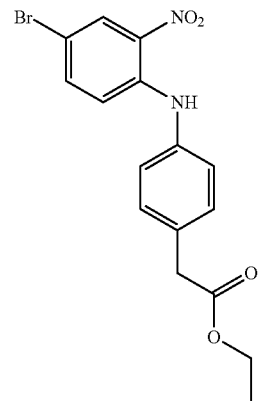

Example 2. Preparation 2—Preparation of Formula IV

Ethyl 2-(4-((4-bromo-2-nitrophenyl)amino)phenyl)acetate (2.026 g, 5.34 mmol) was placed into a 100 mL round bottom flask. EtOH (20 mL) and zinc (3.49 g, 53.4 mmol) were added into the flask, and the reaction mixture was then cooled in an ice bath. Acetic acid (2.246 g, 37.4 mmol) was diluted with EtOH (10 mL), and then added dropwise into the reaction mixture over course of 1 h. The reaction mixture was stirred at 0° C. for 5 h, then filtered and the EtOH evaporated. The reaction mixture was basified with aqueous $NaHCO_3$ and the product was extracted with diethyl ether. The reaction mixture was washed 3× with aqueous $NaHCO_3$ and the organic layer was collected. The organic layer was dried with $MgSO_4$, and the solvent was evaporated to yield ethyl 2-(4-((2-amino-4-bromophenyl)amino)phenyl)acetate 4 as a slight purple solid (1.834 g, 98%). ESMS m/z 349 (M+H)$^+$. The structure of ethyl 2-(4-((2-amino-4-bromophenyl)amino)phenyl)acetate (Formula IV) is shown below:

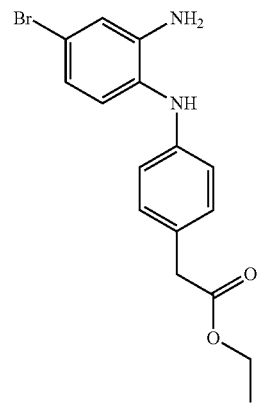

Example 3. Preparation 3—Preparation of Formula V

Ethyl 2-(4-((2-amino-4-bromophenyl)amino)phenyl)acetate (2 g, 5.73 mmol), as prepared above, was placed into a 50 mL round bottle flask. TMOF (15 mL) was added into the flask, followed by pTSA (0.109 g, 0.573 mmol). The reaction mixture was stirred at RT for 3 h. The excess solvent was evaporated and the reaction mixture was washed with aqueous $NaHCO_3$. The product was extracted with ether and the organic layer was washed 2× with aqueous NaHCO$_3$ and 1× with brine. The organic layer was collected, dried, and condensed to yield ethyl 2-(4-(5-bromo-1H-benzo[d]imidazol-1-yl)phenyl)acetate 5 as a brown solid (2.04 g, 99%). ESMS m/z 359 (M+H)$^+$. The structure of ethyl 2-(4-(5-bromo-1H-benzo[d]imidazol-1-yl)phenyl)acetate (Formula V) is shown below:

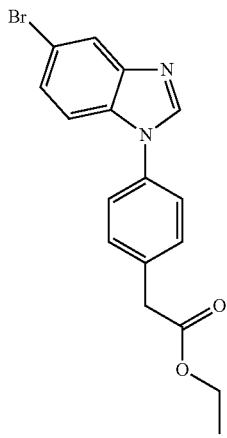

V

Example 4. Preparation 4—Preparation of Formula IX

Ethyl 2-(4-(5-bromo-1H-benzo[d]imidazol-1-yl)phenyl)acetate (4 g, 11.14 mmol), bis(pinacolato)diboron (8.48 g, 33.4 mmol), and KOAc (3.28 g, 33.4 mmol) were dissolved in dioxane (100 mL). The reaction mixture was degassed with N$_2$ for 10 min, and Pd$_2$(dba)$_3$ (0.102 g, 0.111 mmol) and P(Cy)$_3$ (0.094 g, 334 mmol) were added. The tube was sealed and heated under positive N$_2$ pressure to 85° C. for 12 h or until all starting material was consumed based on TLC and LC-MS. The solvent was evaporated and the product was absorbed onto silica. The compound was purified with flash chromatography to yield compound ethyl 2-(4-(5-(4,4,5,5-tetramethyl-1,3,2-dioxaborolan-2-yl)-1H-benzo[d]imidazol-1-yl)phenyl)acetate 9 (4.09 g, 86%). ESMS m/z 407 (M+H)$^{+1}$. The structure of ethyl 2-(4-(5-(4,4,5,5-tetramethyl-1,3,2-dioxaborolan-2-yl)-1H-benzo[d]imidazol-1-yl)phenyl)acetate (Formula IX) is shown below:

IX

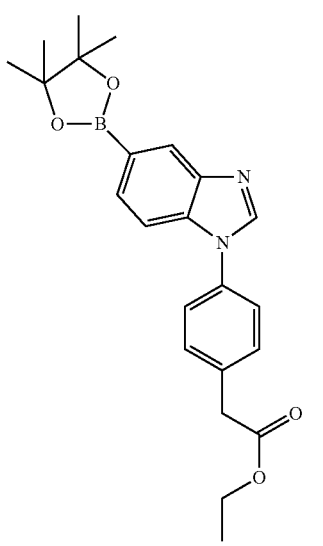

Example 5. Preparation 5—Preparation of Formula VI

Ethyl 2-(4-((2-amino-4-bromophenyl)amino)phenyl)acetate (800 mg, 2.227 mmol) was placed into a 30 mL CEM microwave vial along with 4:1 DMF/Water (20 mL). 1-methylpyrazole-4-boronic acid pinacol ester (556 mg, 2.67 mmol) was added to the vial along with Na$_2$CO$_3$ (1.168 mg, 11.14 mmol). The reaction vessel was degassed for 10 min with N$_2$, followed by the addition of Pd(dppf)Cl$_2$ (91 mg, 0.111 mmol). The reaction mixture was heated with a microwave reactor at 130° C. for 20 min, and the solvent was evaporated. The reaction residue was absorbed onto silica and the product was purified with flash chromatography to yield compound ethyl 2-(4-(5-(1-methyl-1H-pyrazol-4-yl)-1H-benzo[d]imidazol-1-yl)phenyl)acetate 6 (365 mg, 45.5%). ESMS m/z 361(M+H)$^{+1}$. The structure of ethyl 2-(4-(5-(1-methyl-1H-pyrazol-4-yl)-1H-benzo[d]imidazol-1-yl)phenyl)acetate (Formula VI) is shown below:

VI

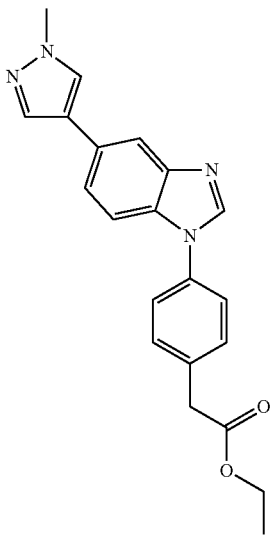

Using the Suzuki coupling procedure as described in the above Preparation 5, the intermediates depicted in the following Table 1 are obtained:

TABLE 1
| Preparation | Product | Starting Material A | Starting Material B | Physical Data |
|---|---|---|---|---|
| 5a | 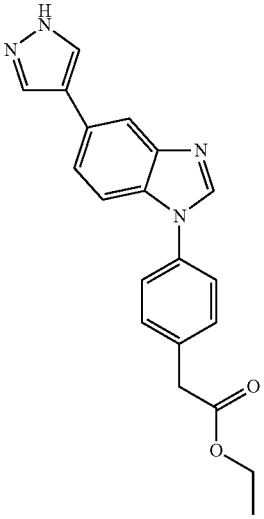 [SMILES: CCOC(=O)Cc1ccc(-n2cnc3cc(-c4cn[nH]c4)ccc32)cc1]<br>Ethyl 2-(4-(5-(1H-pyrazol-4-yl)-1H-benzo[d]imidazol-1-yl)phenyl)acetate | Preparation 3 | (1H-pyrazol-4-yl)boronic acid | MS ES+ m/z 347 (M + 1) |
| 5b | 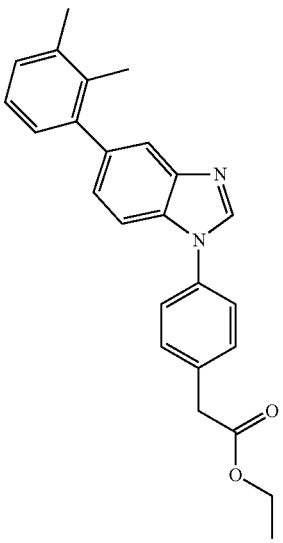 [SMILES: CCOC(=O)Cc1ccc(-n2cnc3cc(-c4cccc(C)c4C)ccc32)cc1]<br>Ethyl 2-(4-(5-(2,3-dimethylphenyl)-1H-benzo[d]imidazol-1-yl)phenyl)acetate | Preparation 3 | (2,3-dimethylphenyl)boronic acid | MS ES+ m/z 385 (M + 1) |

TABLE 1-continued
| Preparation | Product | Starting Material A | Starting Material B | Physical Data |
|---|---|---|---|---|
| 5c | 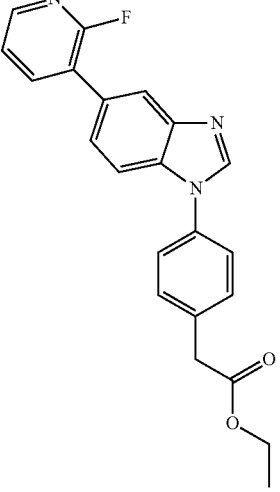<br>Ethyl 2-(4-(5-(2-fluoropyridin-3-yl)-1H-benzo[d]imidazol-1-yl)phenyl)acetate | Preparation 3 | 2-fluoro-3-(4,4,5,5-tetramethyl-1,3,2-dioxaborolan-2-yl)pyridine | MS ES+ m/z 376 (M + 1) |
| 5d | 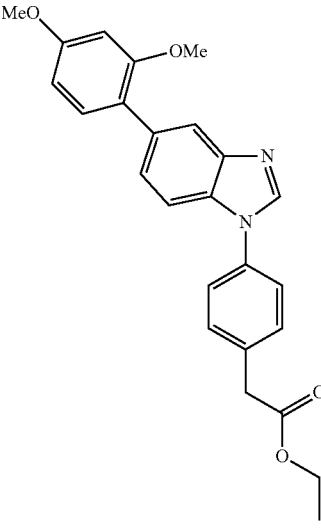<br>Ethyl 2-(4-(5-(2,4-dimethoxyphenyl)-1H-benzo[d]imidazol-1-yl)phenyl)acetate | Preparation 3 | (2,4-dimethoxyphenyl)boronic acid | MS ES+ m/z 417 (M + 1) |

TABLE 1-continued
| Preparation | Product | Starting Material A | Starting Material B | Physical Data |
|---|---|---|---|---|
| 5e | 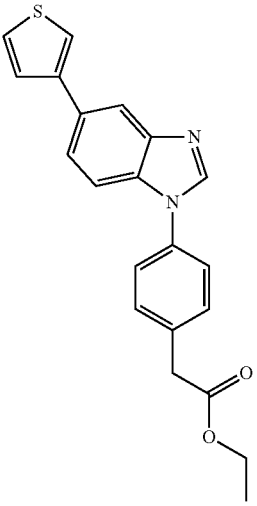 [SMILES: CCOC(=O)Cc1ccc(-n2cnc3cc(-c4ccsc4)ccc32)cc1]<br>Ethyl 2-(4-(5-(thiophen-3-yl)-1H-benzo[d]imidazol-1-yl)phenyl)acetate | Preparation 3 | thiophen-3-ylboronic acid | MS ES$^+$ m/z 363 (M + 1) |
| 5f | 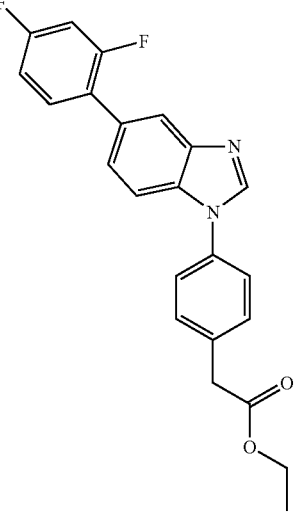<br>Ethyl 2-(4-(5-(2,4-difluorophenyl)-1H-benzo[d]imidazol-1-yl)phenyl)acetate | Preparation 3 | (2,4-difluorophenyl)boronic acid | MS ES$^+$ m/z 393 (M + 1) |

TABLE 1-continued
| Preparation | Product | Starting Material A | Starting Material B | Physical Data |
|---|---|---|---|---|
| 5g | 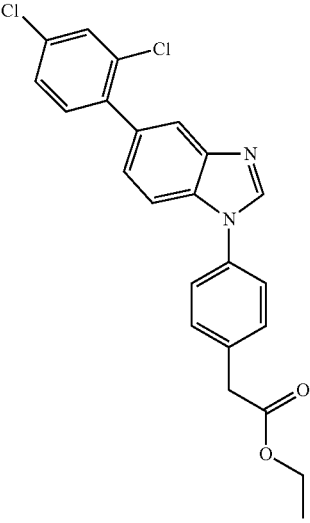 [SMILES: CCOC(=O)Cc1ccc(-n2cnc3cc(-c4ccc(Cl)cc4Cl)ccc32)cc1]<br>Ethyl 2-(4-(5-(2,4-dichlorophenyl)-1H-benzo[d]imidazol-1-yl)phenyl)acetate | Preparation 3 | (2,4-dichlorophenyl)boronic acid | MS ES$^+$ m/z 426 (M + 1) |
| 5h | 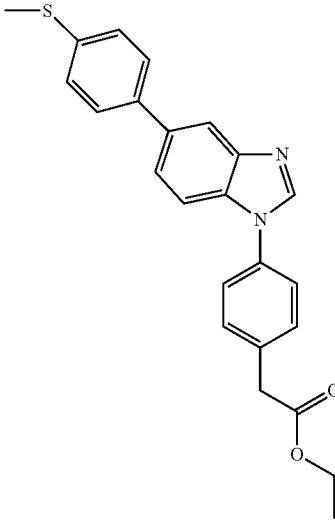<br>Ethyl 2-(4-(5-(4-(methylthio)phenyl)-1H-benzo[d]imidazol-1-yl)phenyl)acetate | Preparation 3 | (4-(methylthio)phenyl)boronic acid | MS ES$^+$ m/z 403 (M + 1) |

TABLE 1-continued
| Preparation | Product | Starting Material A | Starting Material B | Physical Data |
|---|---|---|---|---|
| 5i | 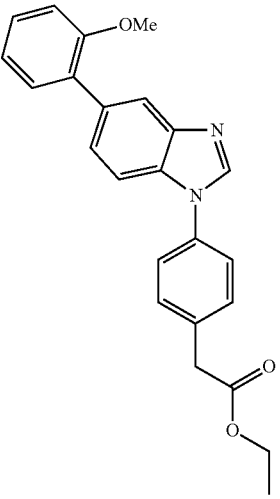 [SMILES: CCOC(=O)Cc1ccc(-n2cnc3cc(-c4ccccc4OC)ccc32)cc1]<br>Ethyl 2-(4-(5-(2-methoxyphenyl)-1H-benzo[d]imidazol-1-yl)phenyl)acetate | Preparation 3 | (2-methoxyphenyl)boronic acid | MS ES$^+$ m/z 387 (M + 1) |
| 5j | 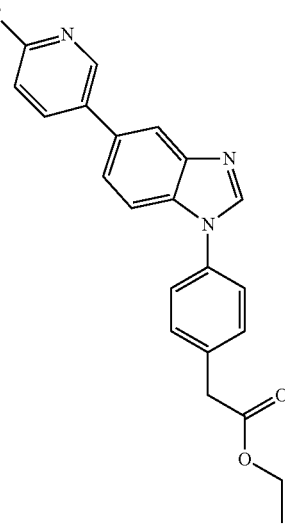<br>Ethyl 2-(4-(5-(6-fluoropyridin-3-yl)-1H-benzo[d]imidazol-1-yl)phenyl)acetate | Preparation 3 | (6-fluoropyridin-3-yl)boronic acid | MS ES$^+$ m/z 376 (M + 1) |

TABLE 1-continued
| Preparation | Product | Starting Material A | Starting Material B | Physical Data |
|---|---|---|---|---|
| 5k | 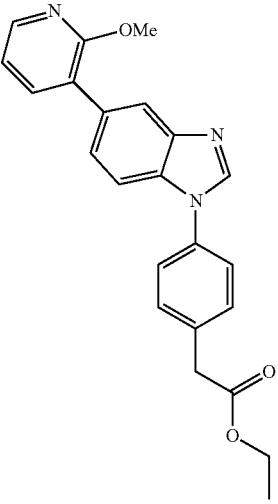<br>Ethyl 2-(4-(5-(2-methoxypyridin-3-yl)-1H-benzo[d]imidazol-1-yl)phenyl)acetate | Preparation 3 | (2-methoxypyridin-3-yl)boronic acid | MS ES+ m/z 376 (M + 1) |
| 5l | 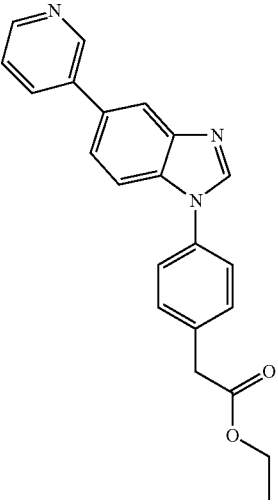 [SMILES: CCOC(=O)Cc1ccc(-n2cnc3cc(-c4cccnc4)ccc32)cc1]<br>Ethyl 2-(4-(5-(pyridin-3-yl)-1H-benzo[d]imidazol-1-yl)phenyl)acetate | Preparation 3 | pyridin-3-ylboronic acid | MS ES+ m/z 358 (M + 1) |

TABLE 1-continued
| Preparation | Product | Starting Material A | Starting Material B | Physical Data |
|---|---|---|---|---|
| 5m | 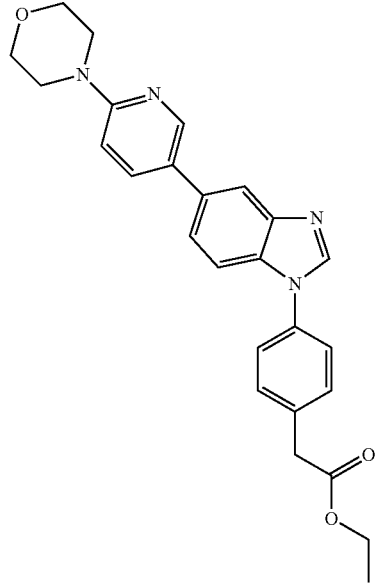 [SMILES: CCOC(=O)Cc1ccc(-n2cnc3cc(-c4ccc(N5CCOCC5)nc4)ccc32)cc1]<br>Ethyl 2-(4-(5-(6-morpholinopyridin-3-yl)-1H-benzo[d]imidazol-1-yl)phenyl)acetate | Preparation 3 | (6-morpholinopyridin-3-yl)boronic acid | MS ES$^+$ m/z 443 (M + 1) |
| 5n | 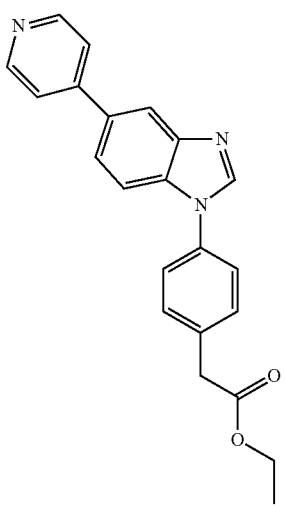 [SMILES: CCOC(=O)Cc1ccc(-n2cnc3cc(-c4ccncc4)ccc32)cc1]<br>Ethyl 2-(4-(5-(pyridin-4-yl)-1H-benzo[d]imidazol-1-yl)phenyl)acetate | Preparation 3 | pyridin-4-ylboronic acid | MS ES$^+$ m/z 358 (M + 1) |

TABLE 1-continued
| Preparation | Product | Starting Material A | Starting Material B | Physical Data |
|---|---|---|---|---|
| 5o | 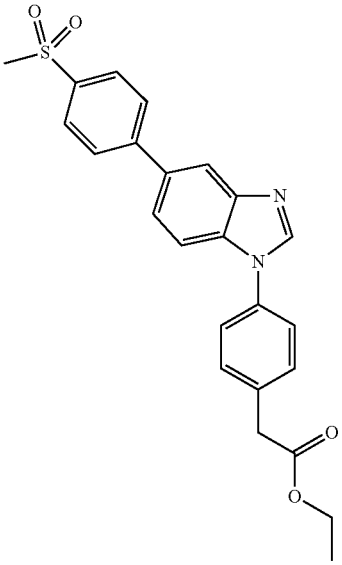 [SMILES: CCOC(=O)Cc1ccc(-n2cnc3cc(-c4ccc(S(C)(=O)=O)cc4)ccc32)cc1]<br>Ethyl 2-(4-(5-(4-(methylsulfonyl)phenyl)-1H-benzo[d]imidazol-1-yl)phenyl)acetate | Preparation 3 | (4-(methylsulfonyl)phenyl)boronic acid | MS ES+ m/z 435 (M + 1) |
| 5p | 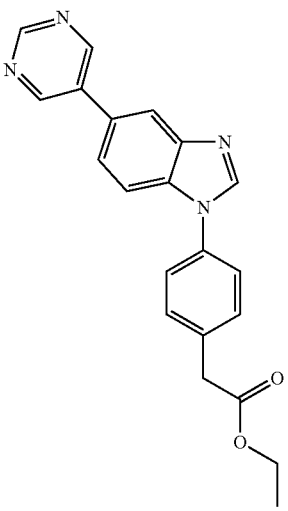 [SMILES: CCOC(=O)Cc1ccc(-n2cnc3cc(-c4cncnc4)ccc32)cc1]<br>Ethyl 2-(4-(5-(pyrimidin-5-yl)-1H-benzo[d]imidazol-1-yl)phenyl)acetate | Preparation 3 | pyrimidin-5-ylboronic acid | MS ES+ m/z 359 (M + 1) |

TABLE 1-continued
| Preparation | Product | Starting Material A | Starting Material B | Physical Data |
|---|---|---|---|---|
| 5q | 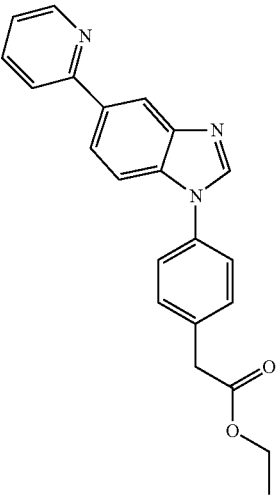 [SMILES: CCOC(=O)Cc1ccc(-n2cnc3cc(-c4ccccn4)ccc32)cc1] Ethyl 2-(4-(5-(pyridin-2-yl)-1H-benzo[d]imidazol-1-yl)phenyl)acetate | Preparation 4 | 2-bromopyridine | MS ES+ m/z 358 (M + 1) |
| 5r | 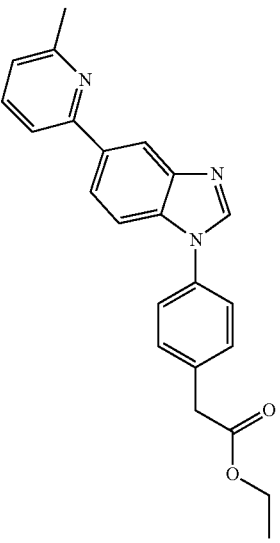 [SMILES: CCOC(=O)Cc1ccc(-n2cnc3cc(-c4cccc(C)n4)ccc32)cc1] Ethyl 2-(4-(5-(6-methylpyridin-2-yl)-1H-benzo[d]imidazol-1-yl)phenyl)acetate | Preparation 4 | 2-bromo-6-methylpyridine | MS ES+ m/z 372 (M + 1) |

TABLE 1-continued

| Preparation | Product | Starting Material A | Starting Material B | Physical Data |
|---|---|---|---|---|
| 5s | Ethyl 2-(4-(5-phenyl-1H-benzo[d]imidazol-1-yl)phenyl)acetate | Preparation 4 | iodobenzene | MS ES+ m/z 357 (M + 1) |

Example 6. Preparation 6—Preparation of Formula VII

LiOH (72.5 mg, 3.03 mmol) was added to a 30 mL CEM microwave vial along with $H_2O$ (4 mL). Ethyl 2-(4-(5-(1-methyl-1H-pyrazol-4-yl)-1H-benzo[d]imidazol-1-yl)phenyl)acetate (365.3 mg, 1.014 mmol) was dissolved in THF (4 mL) and transfered to the microwave vial. The reaction mixture was heated in a microwave at 100° C. for 10 min, the completion of hydrolysis was verified by TLC and LC-MS, and all solvent was evaporated. The reaction mixture was reconstituted in $H_2O$ and washed once with DCM. The aqueous layer was then condensed to yield the compound lithium 2-(4-(5-(1-methyl-1H-pyrazol-4-yl)-1H-benzo[d]imidazol-1-yl)phenyl)acetate 7 (302 mg, 90%). ESMS m/z 331 $(M-Li)^{-1}$. The structure of lithium 2-(4-(5-(1-methyl-1H-pyrazol-4-yl)-1H-benzo[d]imidazol-1-yl)phenyl)acetate (Formula VII) is shown below:

VII

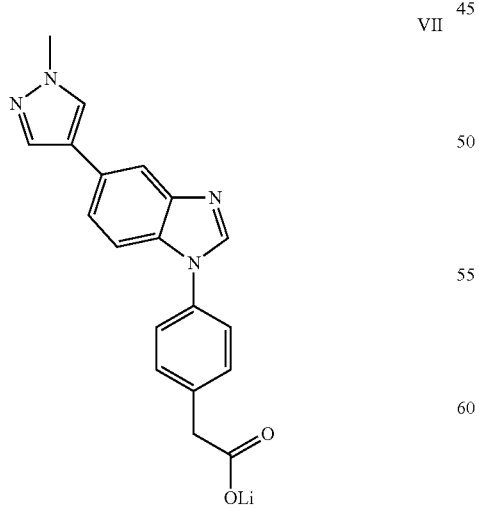

Using the hydrolysis procedure as described in Preparation 6 above, the intermediates listed in the following Table 2 are obtained:

TABLE 2

| Preparation | Product | Starting Material A | Reaction condition | Physical Data |
|---|---|---|---|---|
| 6a | 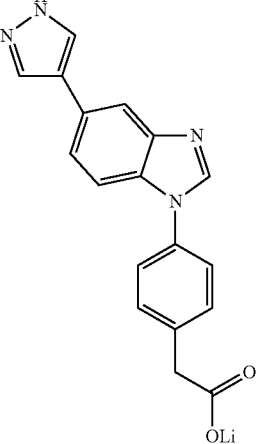<br>Lithium 2-(4-(5-(1H-pyrazol-4-yl)-1H-benzo[d]imidazol-1-yl)phenyl)acetate | Preparation 5a | | MS ES⁻ m/z 317 (M − Li) |
| 6b | 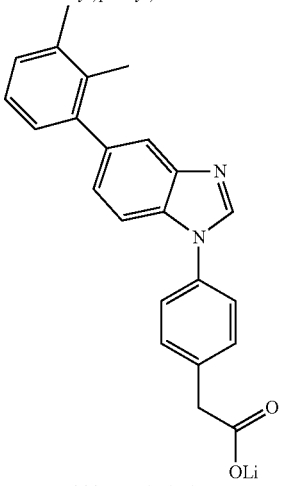<br>Lithium 2-(4-(5-(2,3-dimethylphenyl)-1H-benzo[d]imidazol-1-yl)phenyl)acetate | Preparation 5b | | MS ES⁻ m/z 355 (M − Li) |
| 6c | 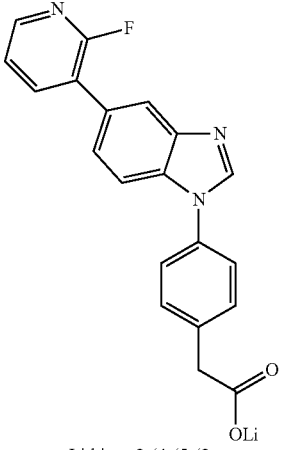<br>Lithium 2-(4-(5-(2-fluoropyridin-3-yl)-1H-benzo[d]imidazol-1-yl)phenyl)acetate | Preparation 5c | | MS ES⁻ m/z 346 (M − Li) |

TABLE 2-continued
| Preparation | Product | Starting Material A | Reaction condition | Physical Data |
|---|---|---|---|---|
| 6d | 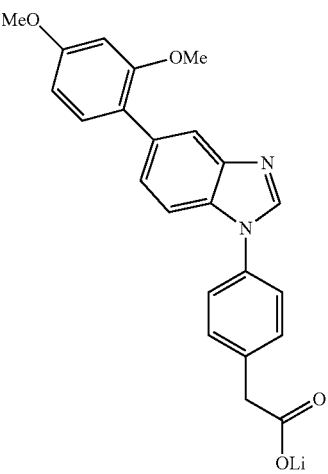  Lithium 2-(4-(5-(2,4-dimethoxyphenyl)-1H-benzo[d]imidazol-1-yl)phenyl)acetate | Preparation 5d | | MS ES⁻ m/z 387 (M − Li) |
| 6e | 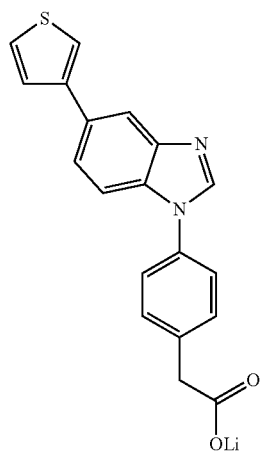  Lithium 2-(4-(5-(thiophen-3-yl)-1H-benzo[d]imidazol-1-yl)phenyl)acetate | Preparation 5e | | MS ES⁻ m/z 333 (M − Li) |

TABLE 2-continued
| Preparation | Product | Starting Material A | Reaction condition | Physical Data |
|---|---|---|---|---|
| 6f | 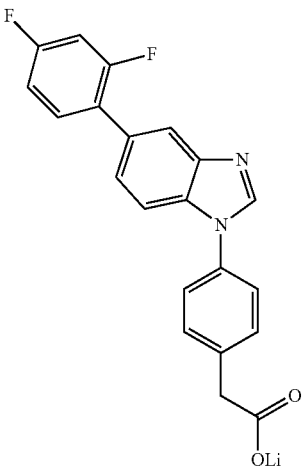<br>Lithium 2-(4-(5-(2,4-difluorophenyl)-1H-benzo[d]imidazol-1-yl)phenyl)acetate | Preparation 5f | | MS ES$^-$ m/z 363 (M − Li) |
| 6g | 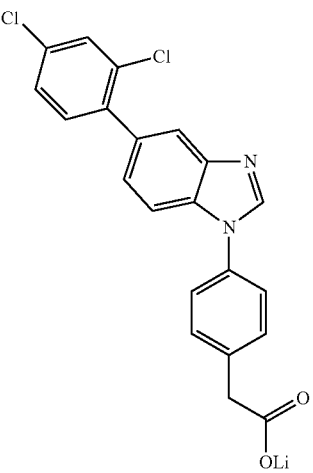<br>Lithium 2-(4-(5-(2,4-dichlorophenyl)-1H-benzo[d]imidazol-1-yl)phenyl)acetate | Preparation 5g | | MS ES$^-$ m/z 395 (M − Li) |

TABLE 2-continued

| Preparation | Product | Starting Material A | Reaction condition | Physical Data |
|---|---|---|---|---|
| 6h | Lithium 2-(4-(5-(4-(methylthio)phenyl)-1H-benzo[d]imidazol-1-yl)phenyl)acetate | Preparation 5h | | MS ES$^-$ m/z 373 (M − Li) |
| 6i | Lithium 2-(4-(5-(2-methoxyphenyl)-1H-benzo[d]imidazol-1-yl)phenyl)acetate | Preparation 5i | | MS ES$^-$ m/z 357 (M − Li) |
| 6j | Lithium 2-(4-(5-(6-fluoropyridin-3-yl)-1H-benzo[d]imidazol-1-yl)phenyl)acetate | Preparation 5j | | MS ES$^-$ m/z 346 (M − Li) |

TABLE 2-continued
| Preparation | Product | Starting Material A | Reaction condition | Physical Data |
|---|---|---|---|---|
| 6k | 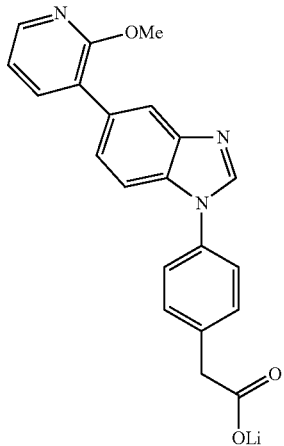<br>Lithium 2-(4-(5-(2-methoxypyridin-3-yl)-1H-benzo[d]imidazol-1-yl)phenyl)acetate | Preparation 5k | | MS ES⁻<br>m/z 358<br>(M − Li) |
| 6l | 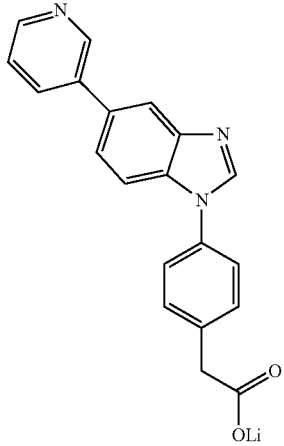<br>Lithium 2-(4-(5-(pyridin-3-yl)-1H-benzo[d]imidazol-1-yl)phenyl)acetate | Preparation 5l | | MS ES⁻<br>m/z 328<br>(M − Li) |

TABLE 2-continued
| Preparation | Product | Starting Material A | Reaction condition | Physical Data |
|---|---|---|---|---|
| 6m | 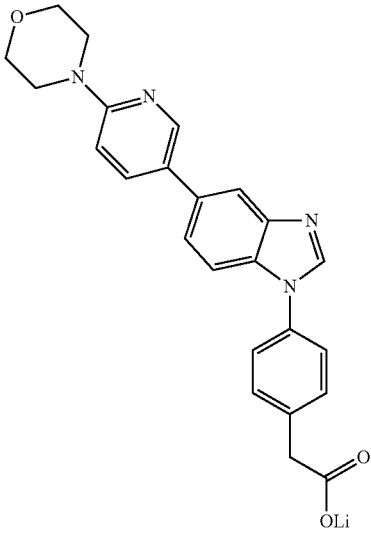<br>Lithium 2-(4-(5-(6-morpholinopyridin-3-yl)-1H-benzo[d]imidazol-1-yl)phenyl)acetate | Preparation 5m | | MS ES⁻ m/z 413 (M − Li) |
| 6n | 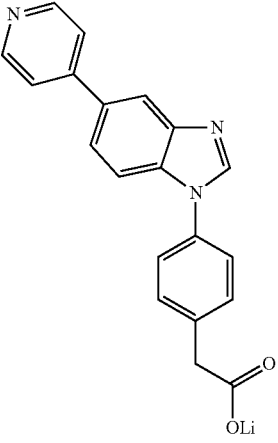<br>Lithium 2-(4-(5-(pyridin-4-yl)-1H-benzo[d]imidazol-1-yl)phenyl)acetate | Preparation 5n | | MS ES⁻ m/z 328 (M − Li) |

TABLE 2-continued

| Preparation | Product | Starting Material A | Reaction condition | Physical Data |
|---|---|---|---|---|
| 6o | 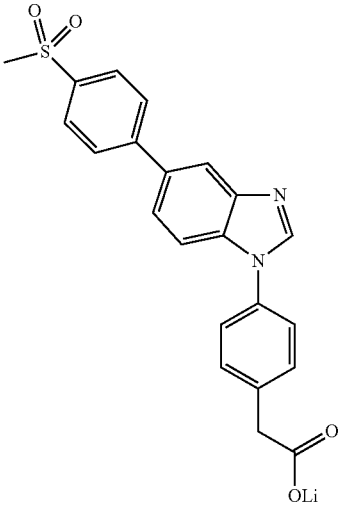<br>Lithium 2-(4-(5-(4-(methylsulfonyl)phenyl)-1H-benzo[d]imidazol-1-yl)phenyl)acetate | Preparation 5o | | MS ES⁻ m/z 405 (M − Li) |
| 6p | 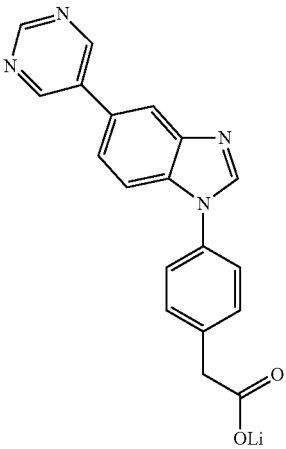<br>Lithium 2-(4-(5-(pyrimidin-5-yl)-1H-benzo[d]imidazol-1-yl)phenyl)acetate | Preparation 5p | | MS ES⁻ m/z 329 (M − Li) |
| 6q | 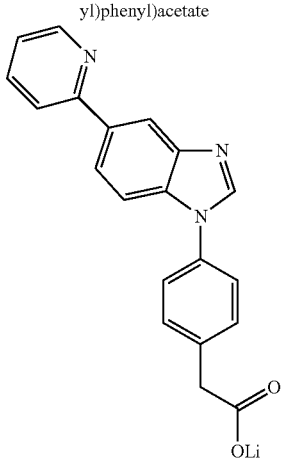<br>Lithium 2-(4-(5-(pyridin-2-yl)-1H-benzo[d]imidazol-1-yl)phenyl)acetate | Preparation 5q | | MS ES⁻ m/z 328 (M − Li) |

TABLE 2-continued

| Preparation | Product | Starting Material A | Reaction condition | Physical Data |
|---|---|---|---|---|
| 6r | Lithium 2-(4-(5-(6-methylpyridin-2-yl)-1H-benzo[d]imidazol-1-yl)phenyl)acetate | Preparation 5r | | MS ES⁻ m/z 342 (M − Li) |
| 6s | Lithium 2-(4-(5-phenyl-1H-benzo[d]imidazol-1-yl)phenyl)acetate | Preparation 5s | | MS ES⁻ m/z 327 (M − Li) |

Example 7. Preparation of Formula VIII

Lithium 2-(4-(5-(1-methyl-1H-pyrazol-4-yl)-1H-benzo[d]imidazol-1-yl)phenyl)acetate (600 mg, 1.805 mmol), EDC (700 mg, 4.51 mmol), HOAt (246 mg, 1.805 mmol), DIPEA (0.377 mL, 2.166 mmol), and 5-(tert-butyl)isoxazol-3-amine (380 mg, 2.71 mmol) were added to a 100 mL round bottom flask. Then, DMF (15 mL) was added to the reaction mixture and the flask was sealed under positive nitrogen pressure and stirred for 12 h at RT (~20-25° C.). At the 12 h time point, all starting material having been consumed was verified by TLC and LC-MS, and the reaction mixture was purified with flash chromatography. The product peak was collected and condensed to yield N-(5-(tert-butyl)isoxazol-3-yl)-2-(4-(5-(1-methyl-1H-pyrazol-4-yl)-1H-benzo[d]imidazol-1-yl)phenyl)acetamide 8 (589.2 mg, 71.8%). ESMS m/z 455 (M+H)$^{+1}$. The structure of N-(5-(tert-butyl)isoxazol-3-yl)-2-(4-(5-(1-methyl-1H-pyrazol-4-yl-1H-benzo[d]imidazol-1-yl)phenyl)acetamide (compound 1: a compound of Formula VIII) is shown below:

Compound 1 - a compound of Formula VIII
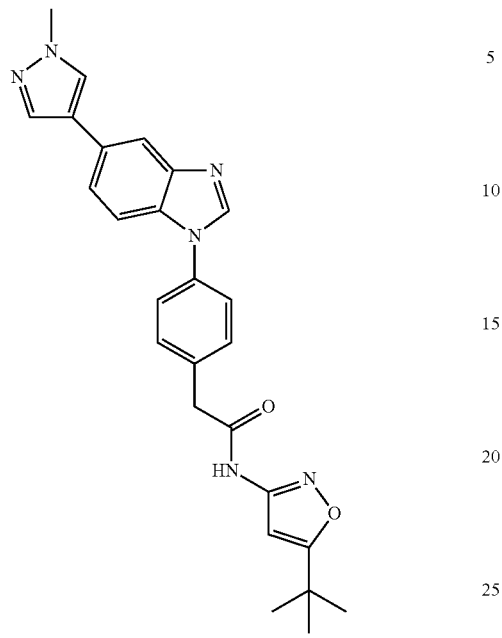
Using the condensation procedure as described in the above Example 1, the intermediates listed in the following Table 3 are obtained:
TABLE 3
| Preparation | product | Starting Material A | Reaction condition | Physical Data |
|---|---|---|---|---|
| 2 | 2-(4-(5-(1H-pyrazol-4-yl)-1H-benzo[d]imidazol-1-yl)phenyl)-N-(5-(tert-butyl)isoxazol-3-yl)acetamide | Preparation 6a | | MS ES⁺ m/z 441 (M + 1) |

TABLE 3-continued
| Preparation | product | Starting Material A | Reaction condition | Physical Data |
|---|---|---|---|---|
| 3 | 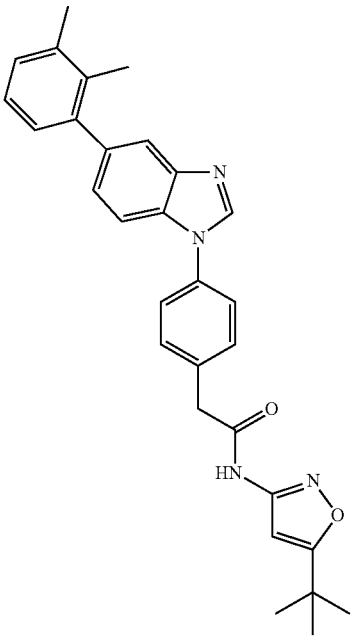 [SMILES: Cc1cccc(-c2ccc3c(c2)ncn3-c2ccc(CC(=O)Nc3cc(C(C)(C)C)on3)cc2)c1C]<br>N-(5-(tert-butyl)isoxazol-3-yl)-2-(4-(5-(2,3-dimethylphenyl)-1H-benzo[d]imidazol-1-yl)phenyl)acetamide | Preparation 6b | | MS ES+ m/z 479 (M + 1) |
| 4 | 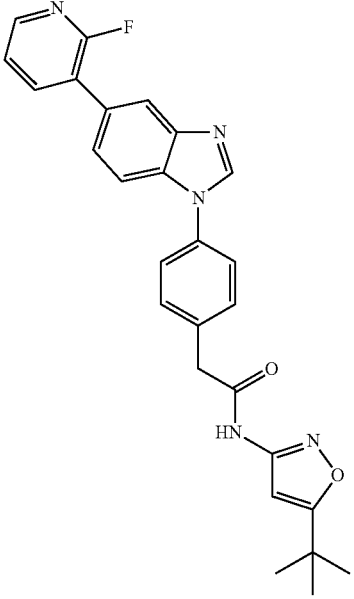 [SMILES: CC(C)(C)c1cc(NC(=O)Cc2ccc(-n3cnc4cc(-c5cccnc5F)ccc43)cc2)no1]<br>N-(5-(tert-butyl)isoxazol-3-yl)-2-(4-(5-(2-fluoropyridin-3-yl)-1H-benzo[d]imidazol-1-yl)phenyl)acetamide | Preparation 6c | | MS ES+ m/z 470 (M + 1) |

TABLE 3-continued
| Preparation | product | Starting Material A | Reaction condition | Physical Data |
|---|---|---|---|---|
| 5 | 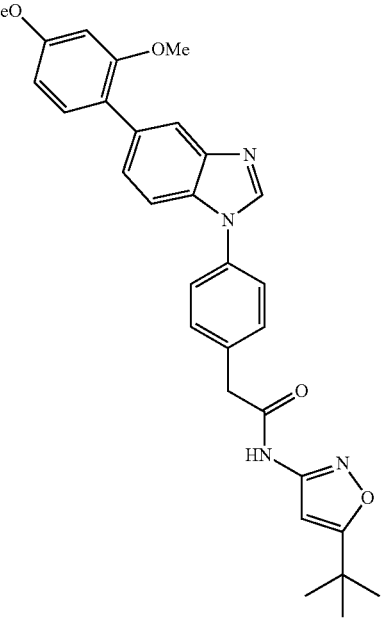 N-(5-(tert-butyl)isoxazol-3-yl)-2-(4-(5-(2,4-dimethoxyphenyl)-1H-benzo[d]imidazol-1-yl)phenyl)acetamide | Preparation 6d | | MS ES+ m/z 511 (M + 1) |
| 6 | 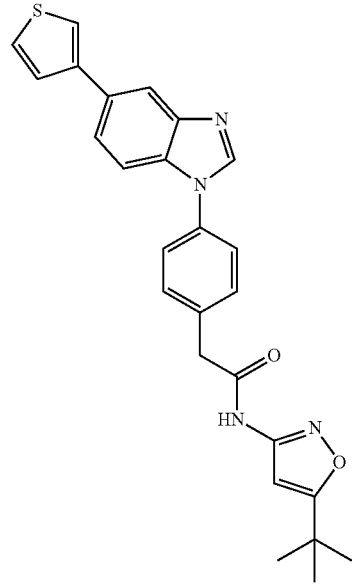 [SMILES: CC(C)(C)c1cc(NC(=O)Cc2ccc(-n3cnc4cc(-c5ccsc5)ccc43)cc2)no1] N-(5-(tert-butyl)isoxazol-3-yl)-2-(4-(5-(thiophen-3-yl)-1H-benzo[d]imidazol-1-yl)phenyl)acetamide | Preparation 6e | | MS ES+ m/z 457 (M + 1) |

TABLE 3-continued
| Preparation | product | Starting Material A | Reaction condition | Physical Data |
|---|---|---|---|---|
| 7 | 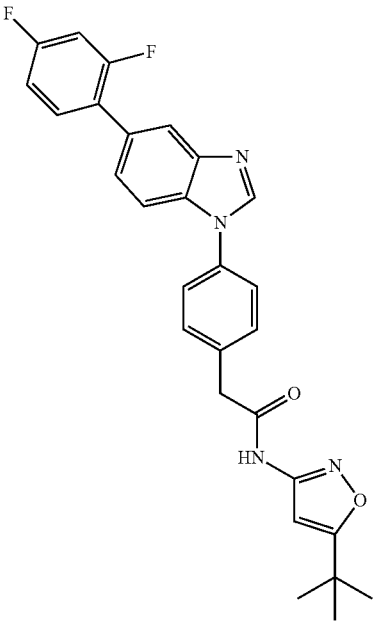 [SMILES: CC(C)(C)c1cc(NC(=O)Cc2ccc(-n3cnc4cc(-c5ccc(F)cc5F)ccc43)cc2)no1] N-(5-(tert-butyl)isoxazol-3-yl)-2-(4-(5-(2,4-difluorophenyl)-1H-benzo[d]imidazol-1-yl)phenyl)acetamide | Preparation 6f | | MS ES$^+$ m/z 487 (M + 1) |
| 8 | 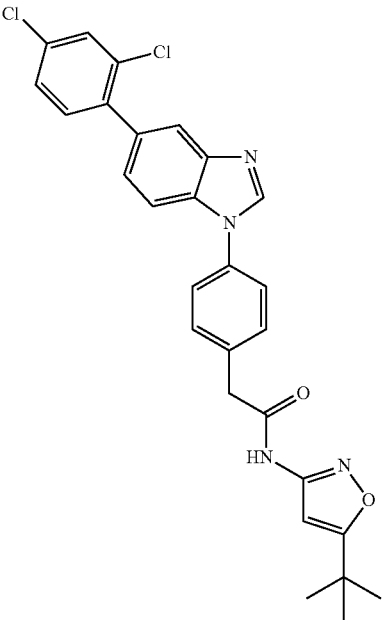 [SMILES: CC(C)(C)c1cc(NC(=O)Cc2ccc(-n3cnc4cc(-c5ccc(Cl)cc5Cl)ccc43)cc2)no1] N-(5-(tert-butyl)isoxazol-3-yl)-2-(4-(5-(2,4-dichlorophenyl)-1H-benzo[d]imidazol-1-yl)phenyl)acetamide | Preparation 6g | | MS ES$^+$ m/z 517 (M + 1) |

TABLE 3-continued
| Preparation | product | Starting Material A | Reaction condition | Physical Data |
|---|---|---|---|---|
| 9 | 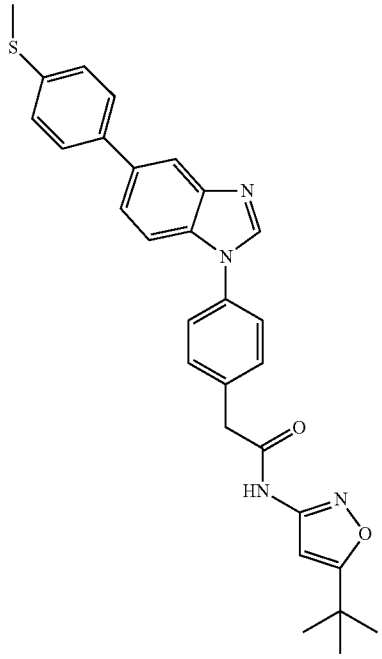 [SMILES: CSc1ccc(-c2ccc3c(c2)ncn3-c2ccc(CC(=O)Nc3cc(C(C)(C)C)on3)cc2)cc1]<br>N-(5-(tert-butyl)isoxazol-3-yl)-2-(4-(5-(4-(methylthio)phenyl)-1H-benzo[d]imidazol-1-yl)phenyl)acetamide | Preparation 6h | | MS ES+ m/z 497 (M + 1) |
| 10 | 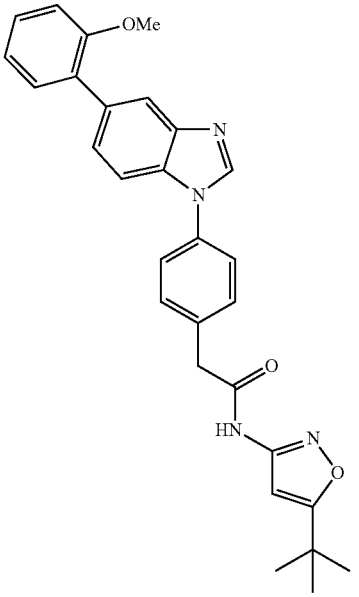 [SMILES: COc1ccccc1-c1ccc2c(c1)ncn2-c1ccc(CC(=O)Nc2cc(C(C)(C)C)on2)cc1]<br>N-(5-(tert-butyl)isoxazol-3-yl)-2-(4-(5-(2-methoxyphenyl)-1H-benzo[d]imidazol-1-yl)phenyl)acetamide | Preparation 6i | | MS ES+ m/z 481 (M + 1) |

TABLE 3-continued
| Preparation | product | Starting Material A | Reaction condition | Physical Data |
|---|---|---|---|---|
| 11 | 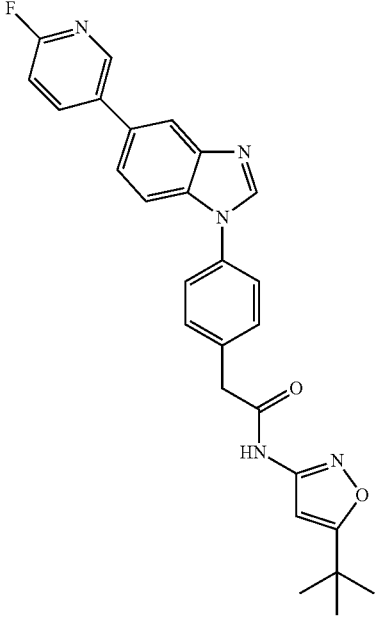<br>N-(5-(tert-butyl)isoxazol-3-yl)-2-(4-(5-(6-fluoropyridin-3-yl)-1H-benzo[d]imidazol-1-yl)phenyl)acetamide | Preparation 6j | | MS ES+ m/z 470 (M + 1) |
| 12 | 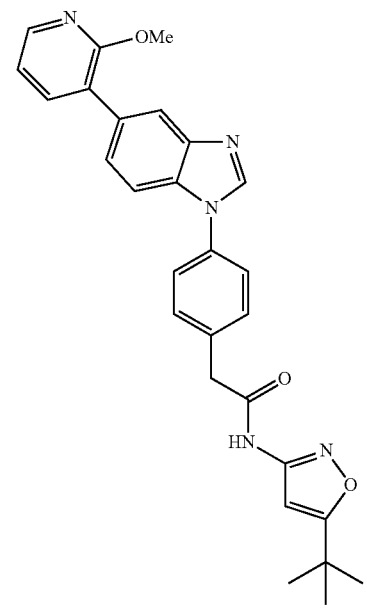 [SMILES: COc1ncccc1-c1ccc2c(c1)ncn2-c1ccc(CC(=O)Nc2cc(C(C)(C)C)on2)cc1]<br>N-(5-(tert-butyl)isoxazol-3-yl)-2-(4-(5-(2-methoxypyridin-3-yl)-1H-benzo[d]imidazol-1-yl)phenyl)acetamide | Preparation 6k | | MS ES+ m/z 482 (M + 1) |

TABLE 3-continued
| Preparation | product | Starting Material A | Reaction condition | Physical Data |
|---|---|---|---|---|
| 13 | 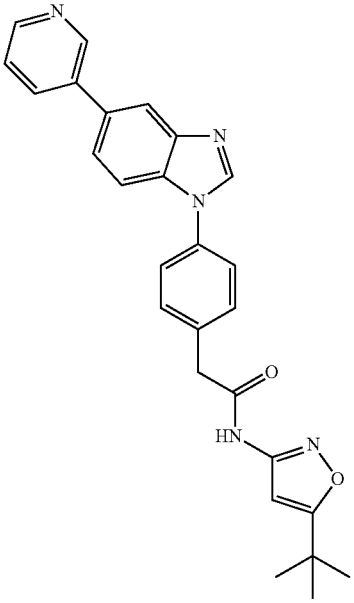 [SMILES: CC(C)(C)c1cc(NC(=O)Cc2ccc(-n3cnc4cc(-c5cccnc5)ccc43)cc2)no1]<br>N-(5-(tert-butyl)isoxazol-3-yl)-2-(4-(5-(pyridin-3-yl)-1H-benzo[d]imidazol-1-yl)phenyl)acetamide | Preparation 6l | | MS ES+ m/z 452 (M + 1) |
| 14 | 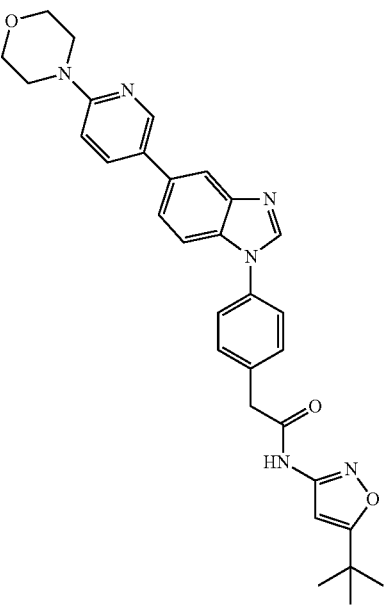 [SMILES: CC(C)(C)c1cc(NC(=O)Cc2ccc(-n3cnc4cc(-c5ccc(N6CCOCC6)nc5)ccc43)cc2)no1]<br>N-(5-(tert-butyl)isoxazol-3-yl)-2-(4-(5-(6-morpholinopyridin-3-yl)-1H-benzo[d]imidazol-1-yl)phenyl)acetamide | Preparation 6m | | MS ES+ m/z 537 (M + 1) |

TABLE 3-continued
| Preparation | product | Starting Material A | Reaction condition | Physical Data |
|---|---|---|---|---|
| 15 | 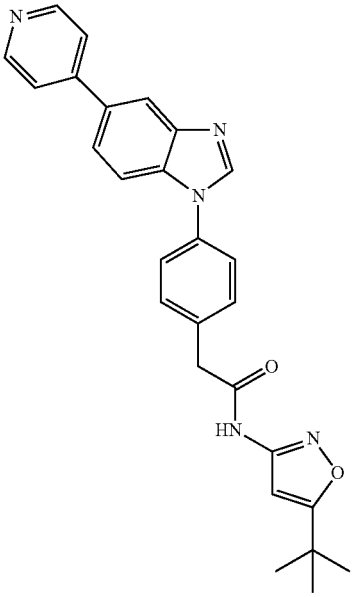<br>N-(5-(tert-butyl)isoxazol-3-yl)-2-(4-(5-(pyridin-4-yl)-1H-benzo[d]imidazol-1-yl)phenyl)acetamide | Preparation 6n | | MS ES⁺ m/z 452 (M + 1) |
| 16 | 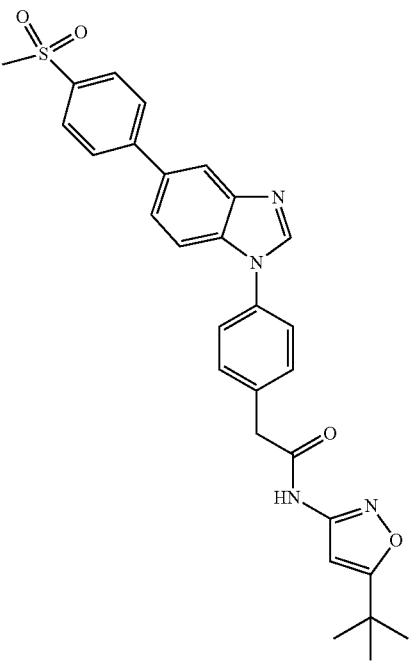 [SMILES: CC(C)(C)c1cc(NC(=O)Cc2ccc(-n3cnc4cc(-c5ccc(S(C)(=O)=O)cc5)ccc43)cc2)no1]<br>N-(5-(tert-butyl)isoxazol-3-yl)-2-(4-(5-(4-(methylsulfonyl)phenyl)-1H-benzo[d]imidazol-1-yl)phenyl)acetamide | Preparation 6o | | MS ES⁺ m/z 529 (M + 1) |

TABLE 3-continued
| Preparation | product | Starting Material A | Reaction condition | Physical Data |
|---|---|---|---|---|
| 17 | 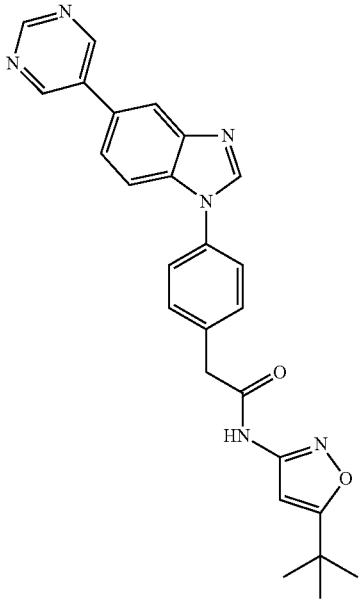 [SMILES: CC(C)(C)c1cc(NC(=O)Cc2ccc(-n3cnc4cc(-c5cncnc5)ccc43)cc2)no1]<br>N-(5-(tert-butyl)isoxazol-3-yl)-2-(4-(5-(pyrimidin-5-yl)-1H-benzo[d]imidazol-1-yl)phenyl)acetamide | Preparation 6p | | MS ES+ m/z 453 (M + 1) |
| 18 | 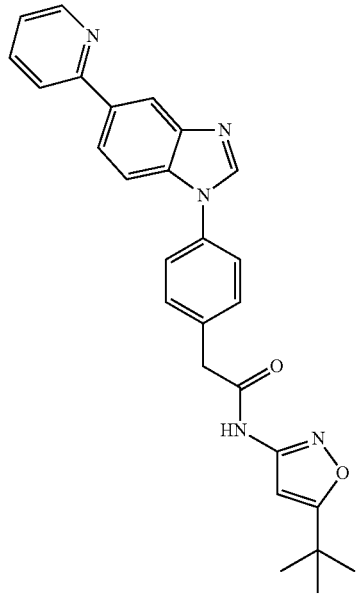 [SMILES: CC(C)(C)c1cc(NC(=O)Cc2ccc(-n3cnc4cc(-c5ccccn5)ccc43)cc2)no1]<br>N-(5-(tert-butyl)isoxazol-3-yl)-2-(4-(5-(pyridin-2-yl)-1H-benzo[d]imidazol-1-yl)phenyl)acetamide | Preparation 6q | | MS ES+ m/z 454 (M + 1) |

TABLE 3-continued

| Preparation | product | Starting Material A | Reaction condition | Physical Data |
|---|---|---|---|---|
| 19 | N-(5-(tert-butyl)isoxazol-3-yl)-2-(4-(5-(6-methylpyridin-2-yl)-1H-benzo[d]imidazol-1-yl)phenyl)acetamide | Preparation 6r | | MS ES+ m/z 468 (M + 1) |
| 20 | N-(5-(tert-butyl)isoxazol-3-yl)-2-(4-(5-phenyl-1H-benzo[d]imidazol-1-yl)phenyl)acetamide | Preparation 6s | | MS ES+ m/z 451 (M + 1) |

Example 8. Discovery of a Dual RET and VEGFR2 Kinase Inhibitor

Establishment of a RET and VEGFR2 Computational Binding Model

The RET protooncogene tyrosine kinase domain has been crystallized with pyrazolopyrimidine PP1 and 4-anilinoquinazoline ZD6474 (vandetanib). These compounds are Type-I inhibitors of protein kinases and have been shown to bind to RET kinase in the DFG-in conformation. The scaffold was determined kinetically to bind the RET kinase in the DFG-out conformation (Type-II) through an incubation based study. A model for DFG-out RET kinase was generated by removing residues SER774 to GLN781 at the back of the allosteric pocket of the crystal structure from ZD6474/RET. This refined DFG-out RET kinase model was used for molecular docking. Discovery Studio 3.5 Visualizer, AutoDock Vina, and AutoDock Tools were used for molecular modeling of potential small molecule inhibitors. The DFG-out model was confirmed to accurately predict binding modes of Type-II inhibitors.

Drug Discovery and Development

Suitable screening assays for RET and VEGFR2 small molecule kinase inhibitors (from a kinase-directed fragment (KDF) library) were established. The RET kinase assay utilizes an EZ Reader Electrophoresis Mobility Chip Instrument (Caliper Life Science). In the assay, 2 nM recombinant RET enzyme (Invitrogen) is pre-incubated with a small molecule inhibitor or control buffer for 30 min to allow the Type-II kinase inhibitor to trap the DFG-out conformation to which the inhibitors bind. This class of inhibitors is indirectly competitive with ATP, and slow binding kinetics (low $k_d$) allow the inhibitors to appear non-competitive and pseudo-irreversible in nature. Because of the non-competitive nature of these inhibitors, a more biologically relevant concentration of ATP substrate (200 µM) was incorporated in this assay. After 30 min of pre-incubation, a substrate mix containing 200 µATP, 20 mM $MgCl_2$ and 1.5 µM fluorescently labeled RET substrate peptide (Caliper LS, peptide 22; Perkin Elmer, USA) was added. The conversion level of the RET substrate peptide was then determined utilizing the EZ Reader instrument. Similarly, VEGFR2 and RET/V804M kinase assays have also been established using the same peptide substrate.

Since the ATP active site of RET and VEGFR2 are highly homologous, the screening and optimization was primarily focused on RET. VEGFR2 activity was measured only on potent RET inhibitors to determine the selectivity. An imidazole analogue was identified through a fragment (and/or privilege structure, molecular weight: less than 300) screening that used a concentration of ATP of 200 µM to avoid non-specific binding and false positives. The homology modeling of RET kinase with the known VEGFR-2 crystal structure determined that the DFG pocket of RET kinase would be easily accessible with an addition of a lipophilic group such as a meta-trifluoromethylphenyl group. The combination of the structure-activity relationship (SAR) information and further optimization of substitutions at both the DFG pocket and the 5 position of benzimidazole furnished the clinical candidate, Pz-1 (N-(5-(tert-butyl)isoxazol-3-yl)-2-(4-(5-(1-methyl-1H-pyrazol-4-yl)-1H-benzo[d]imidazol-1-yl)phenyl)acetamide, with activity in the biochemical assay and an $IC_{50}$ of less than 1 nM for RET wild type, gatekeeper mutant RETV804M, and also for VEGFR2. The exact potency of Pz-1 was beyond the measurable limit of the biochemical assay.

The activity of pRET and pVEGFR2 was determined in cell-based assays, and both phospho-biomarkers were inhibited equi-potently by Pz-1. The activity for the inhibition of auto-RET phosphorylation (in the TT cell line) and auto-VEGFR2 phosphorylation (in the HEK293 cell line) shown in FIG. 3 and FIG. 4, respectively, indicated a strong correlation with the RET and VEGFR2 biochemical assays. The clinical candidate Pz-1 inhibited 90% RET and VEGFR2 auto-phosphorylation at nanomolar concentrations in all cell lines and mutations tested (FIGS. 1-4).

Mechanism of Action and Global Kinase Selectivity

Figure 2:
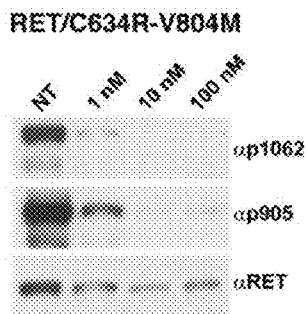
FIG. 2: Photographs of blots showing inhibition of phosphorylation of gate-keeper RET point mutant and rearranged RET oncoproteins by Pz-1 or vehicle (NT: not treated). HEK293 cells were transiently transfected with vectors expressing RET/C634R-V804M mutant (V804 is the gatekeeper RET residue), or RET/PTC1 (CCDC6-RET, found in papillary thyroid carcinoma and lung adenocarcinoma), RET/PTC3 (NCOA4-RET, found in papillary thyroid carcinoma and lung adenocarcinoma), or KIF5B-RET (found in lung adenocarcinoma). After 36 hr from transfection, cells were serum-starved for 12 hr and then treated for 2 hr with indicated concentrations of Pz-1. 50 μg of total cell lysates were subjected to immunoblotting with anti-phospho-Y1062 (αp1062) and anti-phospho-Y905 (αp905) RET antibodies. The blots were normalized using anti-RET (αRET) antibody.
Figure 2:
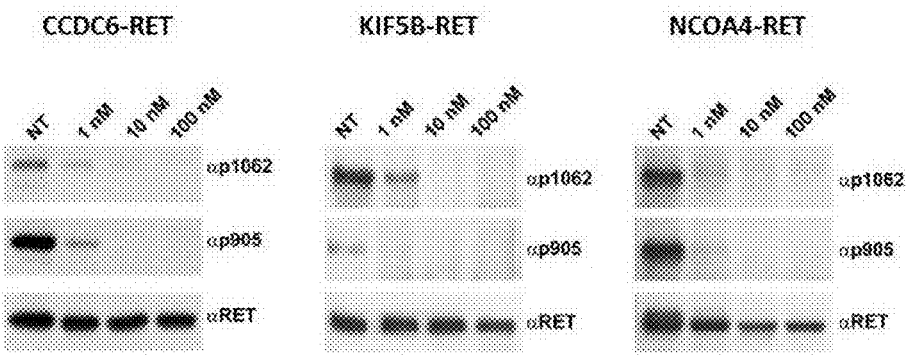
Figure 3:
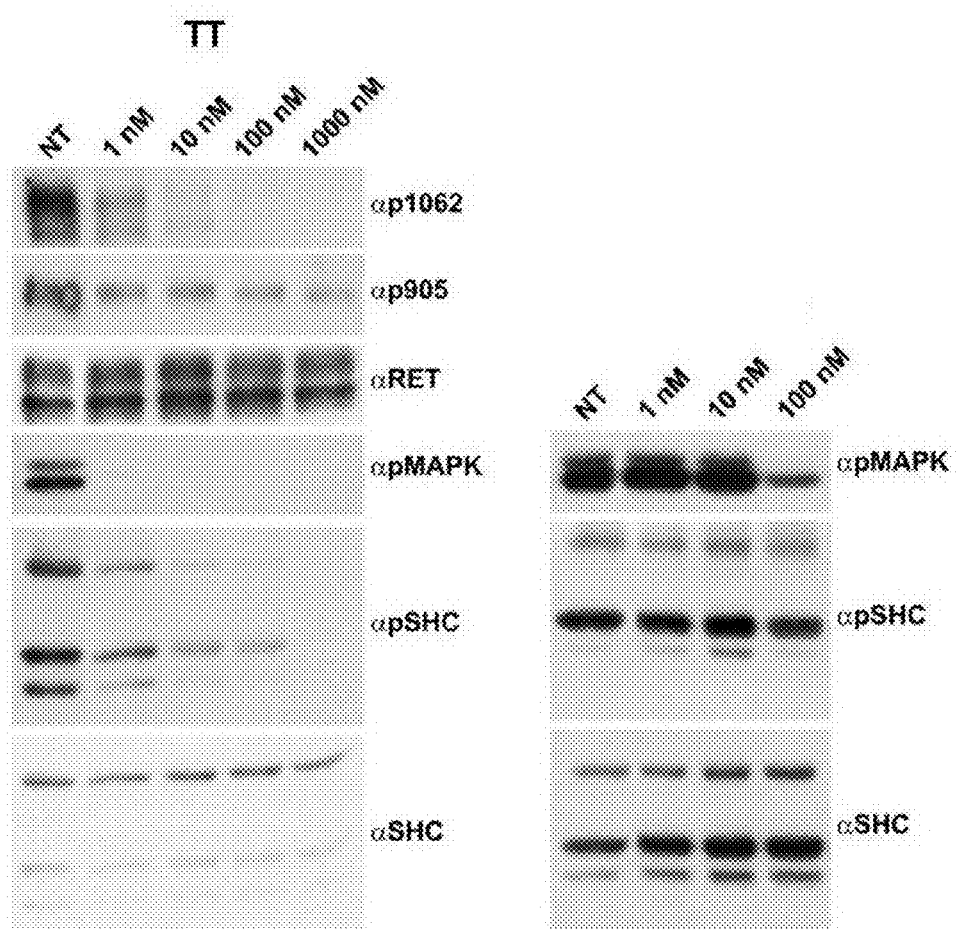
FIG. 3: Photographs of blots showing inhibition of RET protein endogenously expressed in TT cells (human MTC cell line expressing RET/C634W) by indicated concentrations of Pz-1 or vehicle (NT: not treated) and reduced effects in thyroid non-transformed Nthy-ori-3-1 cells. Serum-starved human TT and thyroid non-transformed Nthy-ori-3-1 cell lines were treated for 2 hr with indicated concentrations of Pz-1. 50 μg of total cell lysates were subjected to immunoblotting with anti-phospho-Y1062 (αp1062) and anti-phospho-905 (αpY905) RET antibodies, anti-phospho-MAPK (αpMAPK, T302/Y304), and anti-phospho-SHC (αpSHC, Y317) antibodies. The blots were normalized using anti-RET (αRET) and anti-SHC (αSHC).
Figure 4:
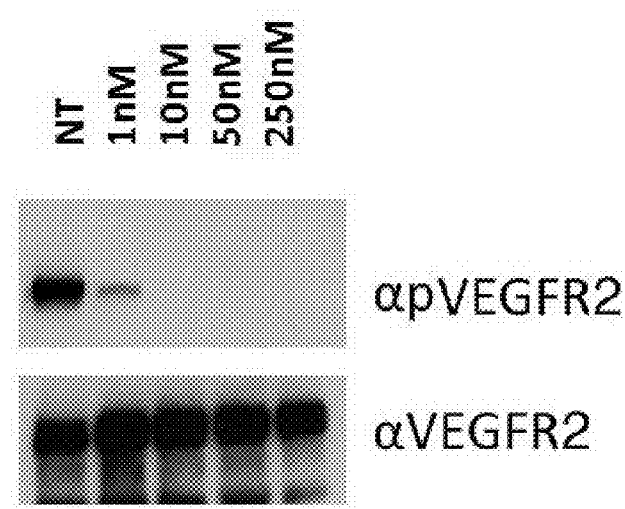
FIG. 4: Photograph of blot showing inhibition of VEGFR2 phosphorylation ectopically expressed in HEK293 cells by indicated doses of Pz-1 or vehicle (NT: not treated). HEK293 cells were transiently transfected with vector expressing VEGFR2. 36 hr following transfection, cells were serum-starved for 12 hr, treated for 2 hr with indicated concentrations of Pz-1 and finally treated with VEGF-A (100 ng/ml) for 15 min. 50 µg of total cell lysates were subjected to immunoblotting with anti-phospho-Y1175 (αpVEGFR2) VEGFR2 antibodies. The blot was normalized using anti-VEGFR2 (αVEGFR2) antibody.

Pz-1 was exceptionally potent on RET and all tested RET mutants including gatekeeper mutants RET/V804M at less than 1 nM (FIGS. 1-3). The RET biochemical assay described herein was not suitable to determine activity of inhibitors having an $IC_{50}$ of less than 1 nM, as the concentration of the RET enzyme in the assay was 2 nM. An intermediate compound was therefore used for the kinetics studies. Prolonging the incubation time from 5 min to 20 min or 60 min resulted in a 3-fold increase of $IC_{50}$ (100 nM to 30 nM), indicating a conformational change of the DFG-in to the DFG-out, the standard feature of a type II kinase inhibitor. Pz-1 was screened at concentration of 50 nM against 91 kinases in KINOMEscan, representing a diversity of each Kinome cluster. The kinase assays in KINOMEScan were more sensitive than the biochemical assays described above. Although there are five kinases (TRKB, TRKC, GKA, FYN, and SRC) active with ~90% inhibition, Pz-1 was still significantly selective against these kinases based on the potent cellular data (strong inhibition of pRET at 1 nM), indicating a good global Kinome selectivity.

Inhibition of pRET and pVEGFR2 Activity by Pz-1 in Cell-Based Assays

The inhibition of RET auto-phosphorylation by Pz-1 was measured in several different cell lines including NIH3T3 fibroblasts expressing RET/C634Y or RET/M918T, TT expressing RET/C634W (MTC), Nthy-ory-3-1 (thyroid, non-transformed with RET; negative control), HEK293/RET/PTC1 (CCDC6-RET that can be found in PTC & lung cancer), HEK293/RET-KIF5B (that can be found in lung cancer), HEK293/RET/PTC3 (NCOA4-RET, that can be found in PTC & lung cancer), and HEK293 transfected with RET/C634R-V804M (FIGS. 1-3). HEK293 cells were transiently transfected with expression vectors comprising the desired mutant. 36 hrs following transfection, cells were serum-starved for 12 hrs and then treated for 2 hrs with Pz-1 at the indicated concentrations, total cell lysates were subjected to immunoblotting with anti-phospho-Y1062 (αp1062) and anti-phospho-Y905 (αp905) RET antibodies. The blots were normalized using anti-RET (αRET) antibody. At 1 nM, Pz-1 strongly inhibited pRET in all cell-lines (FIGS. 1-3), including cells expressing RET/C634R-V804M. Pz-1 at 1 nM also strongly inhibited the VEGFR2 autophosphorylation in HEK 293 cells transiently transfected with VEGFR2 and stimulated with VEGF (FIG. 4). pMAPK is a downstream marker for many kinase pathways and signals through the RAS/MEK/ERK pathway. In the TT cells harbouring RET mutants (FIG. 3), both pMAPK and pRET were similarly strongly inhibited at 1 nM. In contrast, in a thyroid cell line (Nthy-ory-3-1, non-transformed with oncogenic RET), pMAPK was inhibited only at 100 nM (FIG. 3), confirming global kinome selectivity of Pz-1.

Anti-Proliferative Effects of Pz-1 in RET-Driven Cancer Cell Lines

Figure 5:
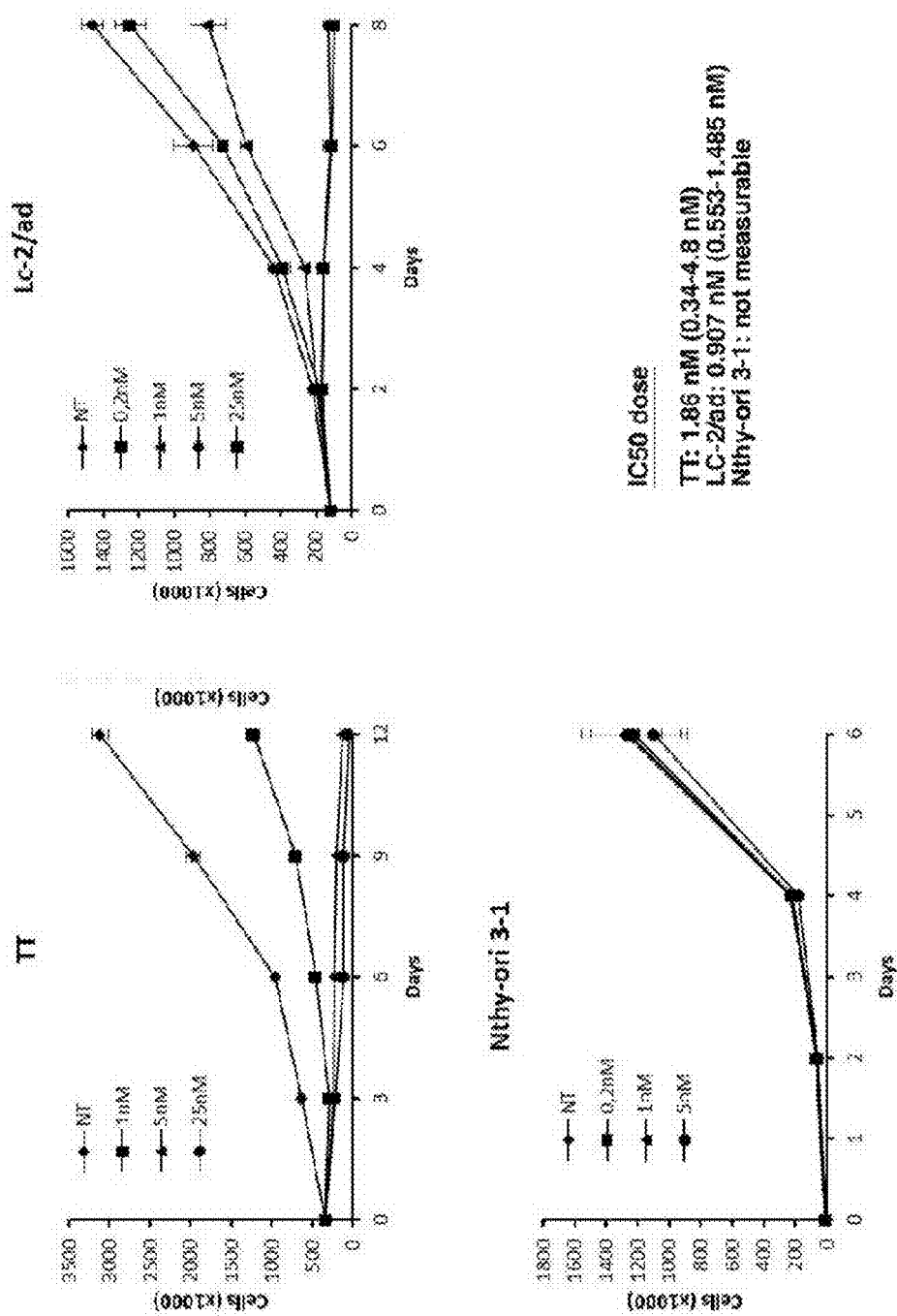
FIG. 5: Effects exerted by indicated concentrations of Pz-1 or vehicle (NT: not treated) on proliferation of TT (human MTC cell line expressing RET/C634W), Lc-2/ad (human NSCLC expressing CCDC6-RET) and Nthy-ori-3-1 (thyroid non-transformed) cell lines. Data are the mean±SD (Standard Deviation) of one experiment performed in triplicate. Bottom, right) Growth inhibition $IC_{50}$ of Pz-1 for the different cell lines: 95% CI (confidence intervals) are indicated in brackets. Cells were seeded in triplicate in 60-mm dishes and kept in 5% (Nthy-ori-3-1) or 10% (TT and Lc-2/ad) fetal calf serum. The day after plating, different concentrations of Pz-1 or vehicle were added to the medium and changed every 2-3 days. Cells were counted every 2-3 days and cell numbers were reported±SD (Standard Deviation). $IC_{50}$ doses (with Confidence Intervals) were calculated through a curve fitting analysis from the last day of growth curves using the PRIZM software program (Graphpad Software Inc).
Figure 6:
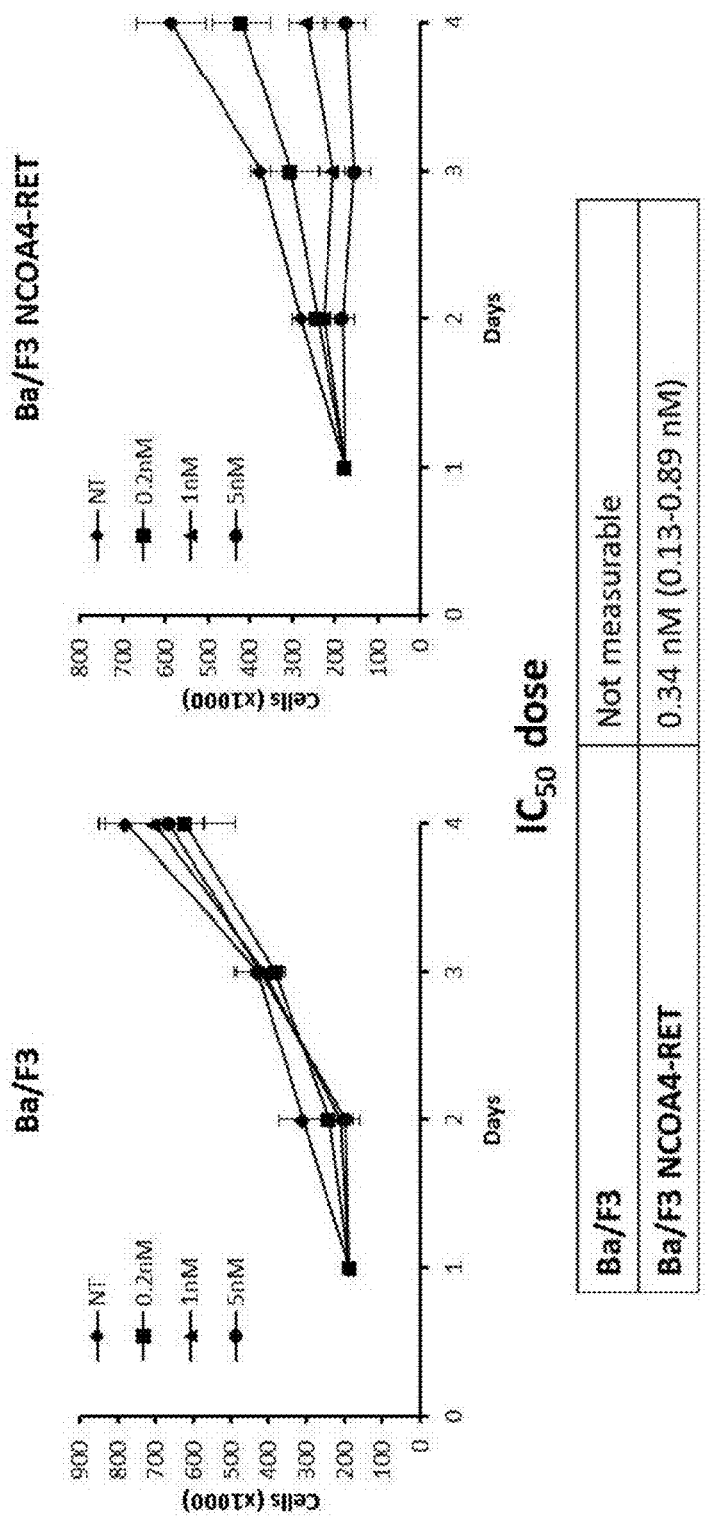
FIG. 6: Activity of Pz-1 on NCOA4-RET oncogene-driven IL-3-independent proliferation of murine Ba/F3 cells. The cell growth curves show inhibition of proliferation by Pz-1 for Ba/F3-NCOA4-RET but not parental Ba/F3. Ba/F3 and Ba/F3 NCOA4-RET cells were incubated with vehicle (NT) or the indicated concentration of Pz-1 in complete medium and counted at different time points. Data are the mean±SD of one experiment performed in triplicate. Murine interleukin-3 (IL-3) dependent pro-B Ba/F3 cells were from ATCC. Ba/F3 cells stably expressing NCOA4-RET (RET/PTC3) protein were generated by transfecting long isoform (RET-51) of NCOA4-RET by electroporation. Parental and Ba/F3-NCOA4-RET cells were cultured in RPMI 1640 with 10% FBS; parental cells required also 10 ng/ml IL-3. $IC_{50}$ doses (with Confidence Intervals) are indicated.

Nthy-ory-3-1 and TTcells were seeded in 60-mm dishes. Cells were kept in 2% (Nthy-ori-3-1) or 10% (TT) fetal calf serum. One day after plating, different concentrations of Pz-1 or vehicle were added to the medium and changed every 2-3 days. Cells were counted every 2-3 days. Ba/F3 cells depend on IL3 for proliferation and lose such a dependency when expressing a constitutively active kinase such as RET. Parental and RET/PTC-expressing Ba/F3 were kept in 10% fetal calf serum in 6-multi wells and counted every day for 4 consecutive days, changing media every 2 days. To compare cell growth, unpaired Student's t test were performed using the Instat software program (Graphpad Software Inc). All p values were two-sided. $IC_{50}$ doses were calculated through a curve fitting analysis from the last day of growth curves using the PRISM software program (Graphpad Software Inc). Pz-1 inhibited cancer cell proliferation driven by RET with an $IC_{50}$ of 1.86 nM for TT cells (FIG. 5), 907 pM for LC-2/ad cells (FIG. 5), and 340 pM for the Ba/F3 cells transfected by RET/PTC3 (FIG. 6). Pz-1 up to 1000 nM did not significantly reduce growth of parental NIH3T3 fibroblasts when used for 3 days, confirming its selectivity.

Determination of In Vivo Target Inhibition (IVTI) of pRET and pVEGFR2, and Efficacy Model.

Figure 7:
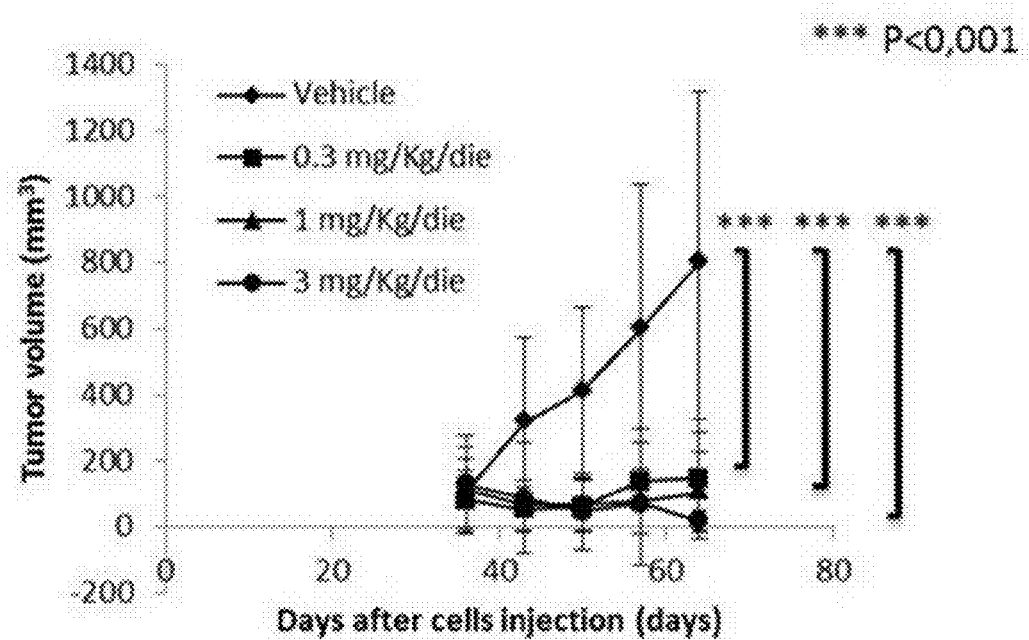
FIG. 7: Anti-tumorigenic activity of Pz-1 on TT cells xenografted into SCID mice. Figure shows the effects of Pz-1 on subcutaneous tumors in SCID mice implanted with TT cells and treated daily by oral gavage with vehicle (n. 10 mice, 18 tumors), or with 0.3, 1.0, or 3.0 mg/kg of Pz-1 (n. 29 mice, 52 tumors). Average volumes of tumors are reported±SD (standard deviation). TT cells ($7.5 \times 10^6$/mouse) were inoculated subcutaneously into dorsal portions (both sides) of 39 female SCID mice (Jackson Laboratories, Bar Harbor, Me.). After 5 weeks, at least one tumour was present in each mouse and a total of 70 tumours were visible: 56 tumours were 40-150 mm³ and 14 tumours were <40 mm³. Tumours were evident on both injection sites in 31 mice; only one site displayed tumour formation in the remaining 8 mice. Tumor-bearing animals were randomly assigned to receive Pz-1 (0.3, 1.0, or 3.0 mg/kg, daily) (29 mice, 52 tumours) or vehicle (10 mice, 18 tumours) by oral gavage. Treatment was administered for 28 consecutive days. Tumor diameters were measured with calipers every week. Tumor volumes (V) were calculated by the rotational ellipsoid formula: $V = A \times B^2/2$ (A=axial diameter; B=rotational diameter) and reported as average volumes±standard deviations. To compare tumor growth, the Kruskal-Wallis test (non parametric ANOVA) and Dunn's Multiple Comparison test was used (InStat program, GraphPad software). P values were statistically significant at $P<0.05$.

TT cells ($7.5 \times 10^6$/mouse) were inoculated subcutaneously into dorsal portions (both sides) of 39 SCID mice (Jackson Laboratories, Bar Harbor, Me.). After 5 weeks, at least one tumor was present in each mouse; tumor-bearing animals were randomly assigned to receive Pz-1 (0.3, 1.0, or 3.0 mg/kg, daily) (29 mice, 52 tumors) or vehicle (10 mice, 18 tumors) by oral gavage. Treatment was administered for 28 consecutive days. Tumor diameters were measured with callipers every week. Tumor volumes (V) were calculated by the rotational ellipsoid formula: $V = A \times B^2/2$ (A=axial diameter; B=rotational diameter) and reported as average volumes±standard deviations. Pz-1 strongly inhibited tumor growth at all tested doses (FIG. 7). Anti-tumorigenic activity of Pz-1 was also assessed in nude mice implanted with RET/C634Y or HRAS(G12V) transformed NIH3T3 fibroblasts. In this case, NIH3T3 RET/C634Y or NIH3T3 HRAS/G12V cells were inoculated subcutaneously into dorsal portion (both sides) of BALB/c nu/nu mice (n. 31 mice/cell line) (Jackson Laboratories, Bar Harbor, Me.). After 4 days, before tumors had appeared, animals were randomly assigned to receive Pz-1 (1.0, 3.0 or 10 mg/kg daily) (23 mice/cell line: 8 mice/group for 1.0 and 3.0 mg/kg daily doses and 7 mice for 10 dose mg/kg daily) or vehicle control (8 mice) by oral gavage. Tumor diameters were measured with calipers every 1-2 days. Tumor volumes (V) were calculated by the rotational ellipsoid formula: $V = A \times B^2/2$ (A=axial diameter; B=rotational diameter) and reported as average volumes±standard deviations. While the treatment totally prevented formation of tumors induced by RET cells, it only reduced, but did not abrogate, formation of tumors driven by the HRAS oncogene (FIG. 8).

Figure 8:
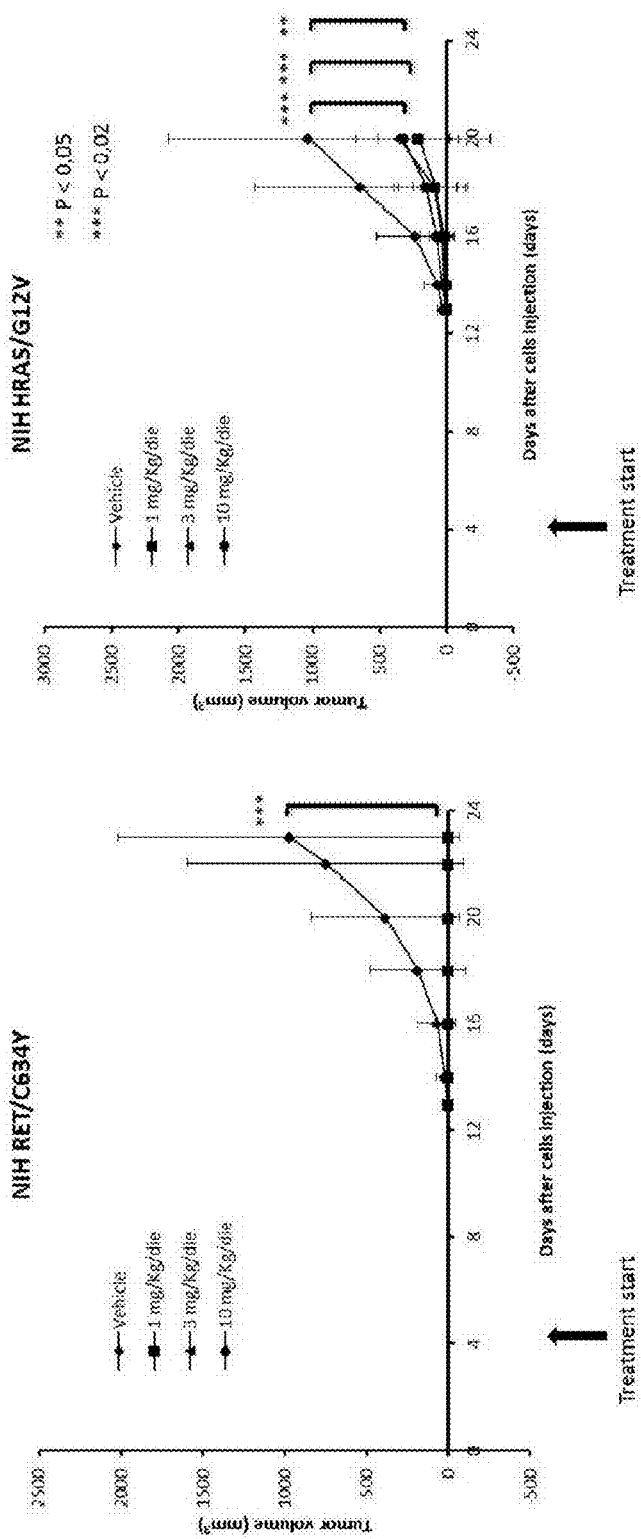
FIG. 8: Anti-tumorigenic activity of Pz-1 in nude mice implanted with RET/C634Y or HRAS(G12V) transformed NIH3T3 fibroblasts. Figure shows the effects of Pz-1 on subcutaneous tumors in mice treated by oral gavage for the indicated time periods with Pz-1 (1.0, 3.0 or 10 mg/kg daily) or vehicle. Average tumor volume (±SD: standard deviations) is reported. NIH3T3 RET/C634Y (200,000 cells) or NIH3T3 HRAS/G12V (50,000 cells) were inoculated subcutaneously into dorsal portion (both sides) of 6-week-old female BALB/c nu/nu mice (n. 31 mice/cell line) (Jackson Laboratories, Bar Harbor, Me.). After 4 days, before tumors had appeared, animals were randomly assigned to receive Pz-1 (1.0, 3.0 or 10 mg/kg daily) (23 mice/cell line: 8 mice/group for 1.0 and 3.0 mg/kg daily doses and 7 mice for 10 dose mg/kg daily) or vehicle control (8 mice) by oral gavage. Tumor diameters were measured with calipers every 1-2 days. Tumor volumes (V) were calculated by the rotational ellipsoid formula and reported as average volumes±standard deviations. To compare tumor growth, the Kruskal-Wallis test (non parametric ANOVA) and Dunn's Multiple Comparison test was used (InStat program, GraphPad software). P values were statistically significant at $P<0.05$.
Figure 9:
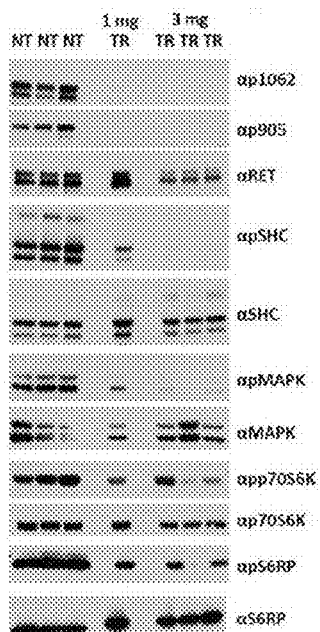
FIG. 9: Photographs of blots showing effects of Pz-1 on cellular phosphorylation events in tumors induced in nude mice (from FIG. 8) by injection of NIH3T3 fibroblasts transformed by RET/C634Y or HRAS/G12V. Blots show inhibition by Pz-1 treatment of pVEGFR2 in both RET/C634Y- and HRAS/G12V-induced tumors and inhibition of RET phosphorylation and of intracellular signaling (SHC, MAPK, p70S6K and S6RP) only in RET/C634Y-induced tumors. Some of the vehicle-treated tumors, at the end of the tumor growth experiment described in FIG. 8, were treated for 48 hr with different doses of Pz-1 (TR) or left untreated (NT). At the end of the treatment, 50 µg of tumor protein lysates were subjected to immunoblotting with anti-phospho-Y1062 (αp1062) and anti-phospho-905 (αpY905) RET antibodies, anti-phospho-MAPK (αpMAPK, T302/Y304), anti-phospho-SHC (αpSHC, Y317), anti-phospho-p70S6K (αpp70S6K, T389), anti-phospho-S6RP (αpS6RP, S235/S236), and anti-phospho-VEGFR2 (αpVEGFR2 pY1175) antibodies. The blots were normalized using anti-RET (αRET), anti-SHC (αSHC), anti-MAPK (αMAPK), anti-p70S6K (αp70S6K), anti-S6RP (αS6RP) or anti-VEGFR2 (αVEGFR2) antibodies.
Figure 9:
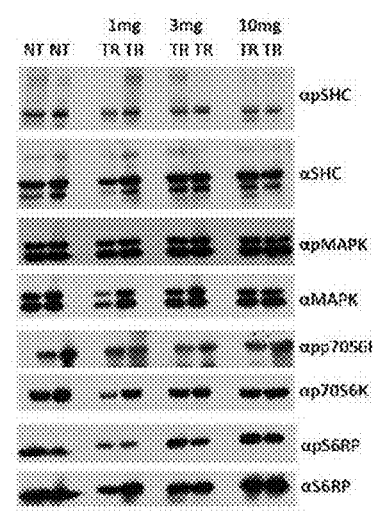
Figure 9:
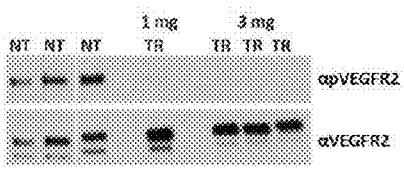
Figure 9:
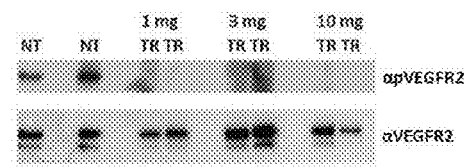
Figure 10:
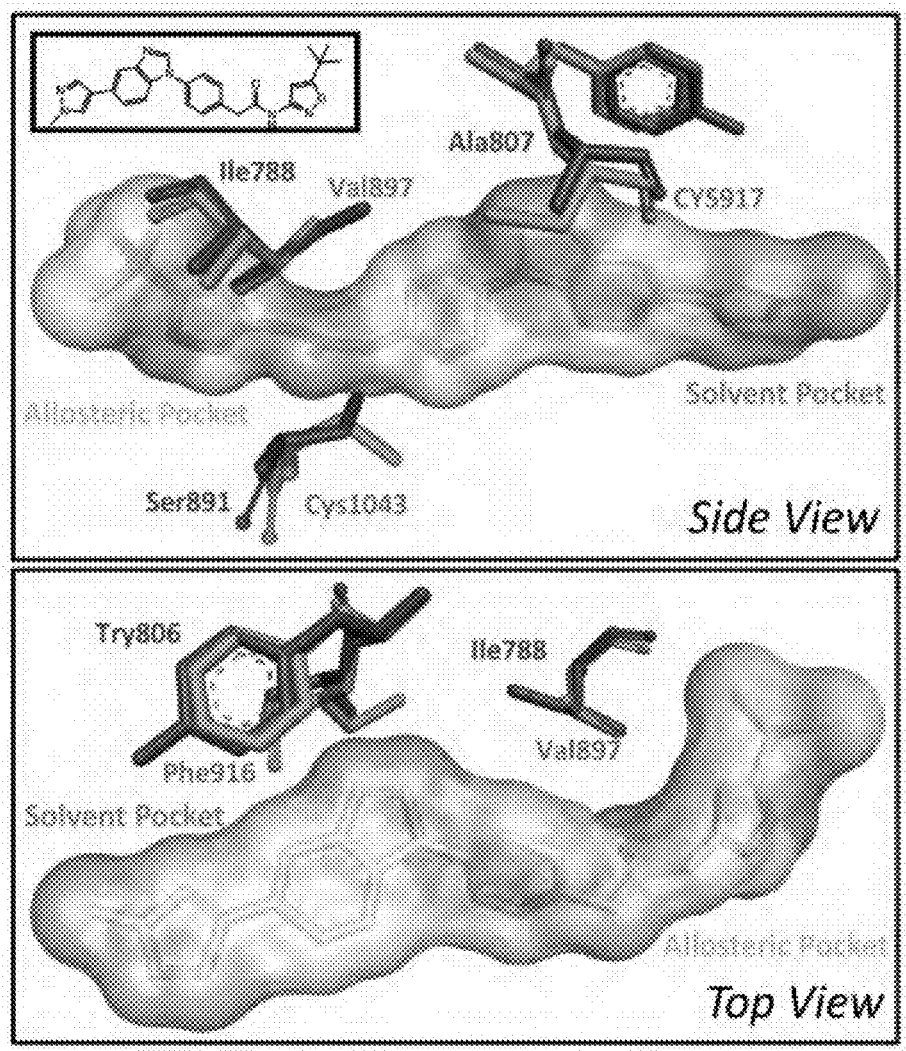
FIG. 10: Docking models of Pz-1 (N-(5-(tert-butyl)isoxazol-3-yl)-2-(4-(5-(1-methyl-1H-pyrazol-4-yl)-1H-benzo[d]imidazol-1-yl)phenyl)acetamide) with RET kinase in red color and VEGFR2 kinase in green color. Four amino-acids are different between RET and VEGFR2, which can be used for the design of selective RET inhibitors. A VEGFR-2 DFG-out crystal structure (PDB#2OH4) and the amino acid sequence of RET (PDB#2IVU) were obtained. Using SWISS-MODEL Automatic Modeling Mode (swissmodel.expasy.org), the RET sequence was employed to build a RET DFG-out homology model using the VEGFR2 DFG-out structure as a template. Using AutoDock Tools: 1) all hydrogens were added as 'Polar Only'; 2) a grid box for the ATP binding site was created (center x=−25.881, center y=9.55, center z=−10.927/size x=16, size y=44, size z=18). Compounds to be computationally modeled were assigned appropriate rotatable bonds using AutoDock Tools. Then, AutoDock Vina was employed to model the compounds. The modeling results were visualized and analyzed with Discovery Studio 3.5.

Some of the vehicle-treated tumors, at the end of the tumor growth experiment reported in FIG. 8, were treated for 48 hr with different doses of Pz-1 (1.0 or 3.0 mg/kg daily) or left untreated. At the end of the treatment, protein lysates were subjected to immunoblotting with anti-phospho-Y1062 ($\alpha$p1062) and anti-phospho-905 ($\alpha$p905) RET antibodies, anti-phospho-MAPK ($\alpha$pMAPK, T302/Y304), anti-phospho-SHC ($\alpha$pSHC, Y317), anti-phospho-p70S6K ($\alpha$pp70S6K, T389), anti-phospho-S6RP ($\alpha$pS6RP, S235/S236), and anti-phospho-VEGFR2 ($\alpha$pVEGFR2, pY1175) antibodies. Pz-1 treatment inhibited pVEGFR2 in both RET/C634Y- and HRAS/G12V-induced tumors and inhibited RET phosphorylation and intracellular signaling (SHC, MAPK, p70S6K and S6RP) only in RET/C634Y-induced tumors (FIG. 9).

Preclinical Formulation, PK, PD, and Toxicology for Pz-1

For PK studies of Pz-1 in animals, a solution formulation for oral administration was created in 500 μL of polysorbate 80, 500 μL of EtOH, and 1.0 mL of pH 2 buffer. For the toxicity studies, a suspension formulation was developed in tween 20 (20%) and xanthan gum (0.125%).

Pz-1 had an AUC of 6.5 μg/hr/mL (solution formulation) and an elimination half-life of 3.8 h at 2 mg/kg in mice. In an oral PK study in rats, Pz-1 showed a high bioavaliblity of 97% with an AUC of 19 μg/hr/mL at 10 mg/kg (oral) and an AUC of 1.9 μg/hr/mL at 1 mg/kg (IV). The elimination half-life in the oral study was 4.2 h with a clearance at 9 mL/min/kg and a volume distribution of 2.02 L/kg. $T_{1/2}$ (3-4 hrs) in rats was in line with $T_{1/2}$ in mice (4.2 hrs).

In vitro, Pz-1 is antiproliferative in MTC TT cell lines harboring $RET^{c634w}$ at an $IC_{50}$ of 1.86 nM and on Ba/F3 cells transfected with oncogenic RET (RET/PTC3) at an $IC_{50}$ of 0.34 nM. Pz-1 was minimally active in the patch clamp hERG assay, with an $IC_{50}$ for the hERG assay of 10 μM (GenScript). The selectivity for RET over hERG is 10,000-fold, which demonstrates a clean cardiovascular toxicity profile. Pz-1 is minimally active on both CYP 2D6, with an $IC_{50}$ of 13.8 μM, and CYP 3A4, with an $IC_{50}$ of 7.4 μM, indicating there were no drug-drug interaction issues with the two major CYP isoforms.

In a week-long toxicology study in mice with a daily dose escalation from 10 mg/kg to 100 mg/kg in the suspension formulation, there was no significant toxicity. The organ pathological analysis in heart, kidney, and liver did not show adverse effects even at a dose of 100 mg/kg. Similarly, the toxicity markers including phosphorus, creatinine, total bilirubin, GGT, ALP, glucose, total protein, albumin, globulin, calcium, cholesterol, and BUN were not impacted at any dose. ALT, a liver toxicity marker, proportionally increased in blood Byrum from 22 U/L at 10 mg/kg, to 51 U/L at 30 mg/kg, and to 96 U/L at 100 mg/kg. At the highest dose, the concentration of ALT was slightly above the normal ALT level of 80 U/L, but below the toxicity threshold of 200 U/L. ALT levels can easily be monitored and can serve as a reversible toxicity marker in the clinical setting.

Example 9. Methods

RET Biochemical Assay

The RET kinase assay utilizes a microfluidics based instrument for direct kinase activity readout (Caliper Life Science). In the assay, 1-2 nM recombinant RET enzyme (Invitrogen) is pre-incubated with the small molecule inhibitor, or control buffer, for 30 min to allow the inhibitor to trap the DFG-out conformation. This class of inhibitors is indirectly competitive with ATP, and slow binding kinetics (very slow $k_{off}$) allows the inhibitors to appear non-competitive and pseudo-irreversible in nature. Because of the non-competitive nature of these inhibitors, a more biologically relevant concentration of ATP substrate was incorporated in this assay. After 30 min of pre-incubation, a substrate mix containing 180-200 μM ATP and 1.0-1.5 μM fluorescently labeled RET substrate peptide (Caliper LS, peptide 22; Perkin Elmer, USA) was added. The conversion level of the RET substrate peptide was determined utilizing the EZ Reader instrument. Final running concentration of buffer components were as follows: 50 mM HEPES, 0.075% (v/v) Brij-35, 0.10% (v/v) polysorbate 20, 0.02% (w/v) $NaN_3$, 10 mM $MgCl_2$, and 2 mM DDT. All compounds exemplified exhibited RET kinase domain with $IC_{50}$ value<1 μM.

VEGFR2 Biochemical Assay

The VEGFR-2 assay was identical to the RET assay except that 1-2 nM recombinant VEGFR-2 was used instead of RET. All compounds exemplified exhibited VEGFR2 kinase domain with $IC_{50}$ value<1 µM.

FLT3 Biochemical Assay

The FLT3 assay was the same as the RET assay except that 1-2 nM recombinant FLT3 was used instead of RET. Also, 1.0-1.5 µM fluorescently labeled FLT3 substrate peptide (Caliper LS, peptide 2; Perkin Elmer, USA) was added in place of peptide 22. All compounds exemplified exhibited FLT3 kinase domain with $IC_{50}$ value<1 µM.

Cell Culture Assays

Fibroblasts transformed by RET oncogenes were cultured in DMEM with 5% calf serum (NIH3T3) or 10% fetal calf serum (RAT1), 2 mM L-glutamine and 100 units/ml penicillin-streptomycin (GIBCO, Paisley, Pa.). HEK 293 cells were grown in DMEM supplemented with 10% fetal calf serum, 2 mM L-glutamine, and 100 units/ml penicillin-streptomycin (GIBCO, Paisley, Pa.). Transient transfections with pcDNA-RET/C634R-V804M, pBABE-RET/PTC1 (CCDC6-RET), -RET/PTC3 (NCOA4-RET), or -KIF5B/RET vectors were carried out with the lipofectamine reagent according to the manufacturer's instructions (GIBCO). The RET constructs used to transfect fibroblasts and HEK 293 encoded the short isoform of the RET protein (RET-9). Parental Ba/F3 and Ba/F3 cells stably expressing RET/PTC3 were cultured in RPMI supplemented with 10% fetal calf serum, 2 mM L-glutamine and 100 units/ml penicillin-streptomycin (GIBCO, Paisley, Pa.). Ba/F3 cells stably expressing RET/PTC3 protein were generated by transfecting long isoform RET/PTC3 (RET-51) by electroporation. Parental cells were grown in the presence of 10 ng/mL IL3. The Nthy-ori-3-1 (NTHY-ORI) cell line, derived from normal thyroid follicular tissue and immortalized by SV40 Large T, was grown in RPMI with 10% fetal calf serum, 2 mM L-glutamine and 100 units/ml penicillin-streptomycin. The TT cell line, derived from a human MTC harboring the RET/C634W mutation (Carlomagno, 1995) was cultured in RPMI with 20% fetal calf serum, 2 mM L-glutamine and 100 units/ml penicillin-streptomycin (GIBCO, Paisley, Pa.).

Immunoblotting and Growth Curve Assays

Protein lysates were prepared according to standard procedures. Briefly, cells were lysed in a buffer containing 50 mM N-2-hydroxyethylpiperazine-N'-2-ethanesulfonic acid (HEPES; pH 7.5), 1% (vol/vol) Triton X-100, 150 mM NaCl, 5 mM EGTA, 50 mM NaF, 20 mM sodium pyrophosphate, 1 mM sodium vanadate, 2 mM phenylmethylsulphonyl fluoride (PMSF), and 1 µg/mL aprotinin. Lysates were clarified by centrifugation at 10,000×g for 15 min. Lysates containing comparable amounts of proteins, estimated by a modified Bradford assay (Bio-Rad, Munich, Germany), were subjected to direct Western blot. Immune complexes were detected with the enhanced chemiluminescence kit (Amersham Pharmacia Biotech, Little Chalfort, UK). Anti-phospho-Shc (#Y317), that recognizes SHC proteins when phosphorylated on Y317, was from Upstate Biotechnology Inc. (Lake Placid, N.Y.). Anti-Shc (H-108) was from Santa Cruz Biotechnology (Santa Cruz, Calif.). Anti-MAPK (#9101) and anti-phospho-MAPK (#9102), specific for p44/42MAPK (ERK1/2) phosphorylated on Thr202/Tyr204, were from Cell Signaling Technologies (Danvers, Mass., USA). Anti-phospho-VEGFR-2/KDR (#2479), specific for VEGFR2/KDR phosphorylated on Tyr1175, and anti-VEGFR-2/KDR (#2478) were from Cell Signaling Technologies (Danvers, Mass., USA). Anti-phospho-S6 ribosomal protein (#2211), specific for S6 ribosomal protein phosphorylated on Ser235-236, anti-S6 ribosomal protein (#2217), anti-p70 S6 kinase (p70S6K) (#2708) and anti-phospho p70 S6 kinase (T389) (#9234) were from Cell Signaling Technologies (Danvers, Mass., USA). Anti-RET is a polyclonal antibody raised against the tyrosine kinase protein fragment of human RET (Santoro, 1995). Anti-phospho905 is a phospho-specific polyclonal antibody recognizing RET proteins phosphorylated at Y905. Anti-phospho1062 is a phospho-specific polyclonal antibody recognizing RET proteins phosphorylated at Y1062. Secondary antibodies coupled to horseradish peroxidase were from Santa Cruz Biotechnology.

$IC_{50}$ Values

For these examples, dose-response growth curves and $IC_{50}$ doses were graphed using the curve-fitting PRISM software (GraphPad Software). An unpaired Student's-t test (InStat program, GraphPad software) was used to compare tumour growth. P values were statistically significant at p<0.05.

Certain embodiments of the compounds and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

We claim:

1. A compound of the Formula VIII

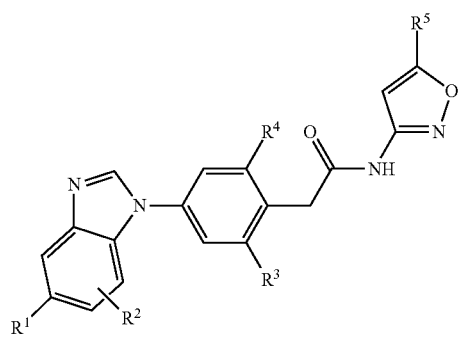

Formula VIII wherein:

$R^1$ is unsubstituted aryl or heteroaryl; or aryl or heteroaryl substituted one with one or two $R^6$ substituents;

$R^2$ is selected from the group consisting of H, $(C_1-C_3)$ alkyl, halo, —CN, —O—$(C_1-C_3)$alkyl, —O—$(CH_2)_nX$, —N$(R^7)(R^8)$, —CONH$(CH_2)_nX$, —SO$_2$NH$(CH_2)_nX$, and —SO$_2(C_1-C_3)$alkyl;

$R^3$ and $R^4$ are each independently H, $(C_1-C_6)$alkyl, or CN;

$R^5$ is —$(C_1-C_4)$ unsubstituted alkyl or $(C_1-C_3)$ alkyl substituted with one to three fluorines;

$R^6$ independently represents one or two of H, OH, $NH_2$, $(C_1-C_3)$alkyl, halo, —CN, —O$(C_1-C_3)$alkyl, —O(CH$_2$)nX, —N(R$^7$)(R$^8$), —CONH$_2$, —CONH(CH$_2$)$_n$X, —SO$_2$NH(CH$_2$)$_n$X, or —SO$_2$(C$_1$-C$_3$)alkyl; X is OR$^9$ or N(R$^7$)(R$^8$);

R$^7$ and R$^8$ are each independently hydrogen or (C$_1$-C$_4$) alkyl or (C$_1$-C$_4$)alkoxy, or R$^7$ and R$^8$ together form a ring; n is 2 or 3; and R$^9$ is H or (C$_1$-C$_3$)alkyl; and salts, stereoisomers, enantiomers, racemates, solvates, hydrates, polymorphs, and prodrugs thereof.

2. A compound of claim 1, wherein the compound is selected from the group consisting of: N-(5-(tert-butyl)isoxazol-3-yl)-2-(4-(5-(1-methyl-1H-pyrazol-4-yl)-1H-benzo[d]imidazol-1-yl)phenyl)acetamide (Pz-1); 2-(4-(5-(1H-pyrazol-4-yl)-1H-benzo[d]imidazol-1-yl)phenyl)-N-(5-(tert-butyl)isoxazol-3-yl)acetamide; N-(5-(tert-butyl)isoxazol-3-yl)-2-(4-(5-(2,3-dimethylphenyl)-1H-benzo[d]imidazol-1-yl)phenyl)acetamide; N-(5-(tert-butyl)isoxazol-3-yl)-2-(4-(5-(2-fluoropyridin-3-yl)-1H-benzo[d]imidazol-1-yl)phenyl)acetamide; N-(5-(tert-butyl)isoxazol-3-yl)-2-(4-(5-(2,4-dimethoxyphenyl)-1H-benzo[d]imidazol-1-yl)phenyl)acetamide; N-(5-(tert-butyl)isoxazol-3-yl)-2-(4-(5-(thiophen-3-yl)-1H-benzo[d]imidazol-1-yl)phenyl)acetamide; N-(5-(tert-butyl)isoxazol-3-yl)-2-(4-(5-(2,4-difluorophenyl)-1H-benzo[d]imidazol-1-yl)phenyl)acetamide; N-(5-(tert-butyl)isoxazol-3-yl)-2-(4-(5-(2,4-dichlorophenyl)-1H-benzo[d]imidazol-1-yl)phenyl)acetamide; N-(5-(tert-butyl)isoxazol-3-yl)-2-(4-(5-(2-methoxyphenyl)-1H-benzo[d]imidazol-1-yl)phenyl)acetamide; N-(5-(tert-butyl)isoxazol-3-yl)-2-(4-(5-(6-fluoropyridin-3-yl)-1H-benzo[d]imidazol-1-yl)phenyl)acetamide; N-(5-(tert-butyl)isoxazol-3-yl)-2-(4-(5-(2-methoxypyridin-3-yl)-1H-benzo[d]imidazol-1-yl)phenyl)acetamide; N-(5-(tert-butyl)isoxazol-3-yl)-2-(4-(5-(pyridin-3-yl)-1H-benzo[d]imidazol-1-yl)phenyl)acetamide; N-(5-(tert-butyl)isoxazol-3-yl)-2-(4-(5-(6-morpholinopyridin-3-yl)-1H-benzo[d]imidazol-1-yl)phenyl)acetamide; N-(5-(tert-butyl)isoxazol-3-yl)-2-(4-(5-(pyridin-4-yl)-1H-benzo[d]imidazol-1-yl)phenyl)acetamide; N-(5-(tert-butyl)isoxazol-3-yl)-2-(4-(5-(4-(methylsulfonyl)phenyl)-1H-benzo[d]imidazol-1-yl)phenyl)acetamide; N-(5-(tert-butyl)isoxazol-3-yl)-2-(4-(5-(pyrimidin-5-yl)-1H-benzo[d]imidazol-1-yl)phenyl)acetamide; N-(5-(tert-butyl)isoxazol-3-yl)-2-(4-(5-(pyridin-2-yl)-1H-benzo[d]imidazol-1-yl)phenyl)acetamide; N-(5-(tert-butyl)isoxazol-3-yl)-2-(4-(5-(6-methylpyridin-2-yl)-1H-benzo[d]imidazol-1-yl)phenyl)acetamide; and N-(5-(tert-butyl)isoxazol-3-yl)-2-(4-(5-phenyl-1H-benzo[d]imidazol-1-yl)phenyl)acetamide.

3. A pharmaceutical composition comprising: a compound of claim 1 or a pharmaceutically acceptable salt thereof; and a pharmaceutically acceptable carrier, diluent, or excipient.

4. The pharmaceutical composition of claim 3, wherein the compound is N (5 (tert-butyl)isoxazol-3-yl)-2-(4-(5-(1-methyl-1H-pyrazol-4-yl)-1H-benzo[d]imidazol-1-yl)phenyl)acetamide (Pz-1), or a pharmaceutically acceptable salt thereof.

5. A method of treating a subject with a RET, TRK (A,B,C) and/or VEGFR2 dependent cancer, the method comprising administering an effective dose of the pharmaceutical composition of claim 3 to a subject in need thereof.

6. The method of claim 5, wherein the pharmaceutical composition is administered in combination with any other anti-cancer agent.

7. The method of claim 5, wherein the RET, TRK (A,B,C,) and/or VEGFR2 dependent cancer is selected from thyroid cancer, lung cancer, or breast cancer.

8. A method of inhibiting phosphorylation of RET comprising treating RET, TRK (A,B,C,) and/or VEGFR2 dependent cancer cells expressing the RET gene with an effective amount of a compound of claim 1.

9. A method of inhibiting phosphorylation of VEGFR2/KDR comprising treating RET, TRK (A,B,C,) and/or VEGFR2 dependent cancer cells expressing the VEGFR protein with an effective amount of a compound of claim 1.

10. A method of inhibiting proliferation of thyroid RET TRK (A,B,C,) and/or VEGFR1 dependent cancer cells comprising treating thyroid RET, TRK (A,B,C,) and/or VEGFR2 dependent cancer cells with an effective amount of a compound of claim 1.

11. The method of claim 10, wherein the thyroid cancer cells comprise MTC.

12. A method of inhibiting the activity of a tyrosine kinase, comprising treating RET, TRK (A,B,C,) and/or VEGFR2 dependent cancer cells with an effective amount of a compound of claim 1.

13. The method of claim 12, wherein the tyrosine kinase is selected from the group consisting of RET, Trk-A, Trk-B, Trk-C, FLT3-ITD, c-Kit, VEGFR, and PDGFR.

14. The method of claim 12, wherein the compound exhibits inhibitory activity of the kinase domain with an IC$_{50}$ value<1 µM.

15. A method of treating RET, TRK (A,B,C,) and/or VEGFR2 dependent cancer-associated pain, comprising administering an effective amount of a pharmaceutical composition of claim 3 to a patient in need thereof.

16. A kit for the preparation of a pharmaceutical composition comprising:
a first container comprising a compound of claim 1; and
a second container comprising a pharmaceutically acceptable carrier, diluent, or excipient.

* * * * *